United States Patent
Lubisch et al.

(10) Patent No.: US 7,781,596 B1
(45) Date of Patent: *Aug. 24, 2010

(54) SUBSTITUTED 2-PHENYLBENZIMIDAZOLES, THE PRODUCTION THEREOF AND THEIR USE

(75) Inventors: Wilfried Lubisch, Heidelberg (DE); Michael Kock, Schifferstadt (DE); Thomas Höger, Edingen-Neckarhausen (DE)

(73) Assignee: Abbott Laboratories, Abbott Park, IL (US)

(*) Notice: Subject to any disclaimer, the term of this patent is extended or adjusted under 35 U.S.C. 154(b) by 0 days.

This patent is subject to a terminal disclaimer.

(21) Appl. No.: 09/830,992

(22) PCT Filed: Oct. 28, 1999

(86) PCT No.: PCT/EP99/08169

§ 371 (c)(1),
(2), (4) Date: May 3, 2001

(87) PCT Pub. No.: WO00/26192

PCT Pub. Date: May 11, 2000

(30) Foreign Application Priority Data

| Nov. 3, 1998 | (DE) | 198 50 709 |
| Nov. 16, 1998 | (DE) | 198 52 801 |
| Mar. 1, 1999 | (DE) | 198 08 733 |

(51) Int. Cl.
*A61K 31/4184* (2006.01)
*A61K 31/496* (2006.01)
*C07D 235/18* (2006.01)
*C07D 403/10* (2006.01)

(52) U.S. Cl. ............ 548/306.1; 548/309.7; 548/310.7; 540/575; 544/370; 546/187; 546/199; 514/211.08; 514/254.06; 514/316; 514/322; 514/394

(58) Field of Classification Search ............ 548/306.1, 548/309.7, 310.7; 514/394, 211.08, 254.06, 514/316, 322; 540/575; 544/370; 546/187, 546/199

See application file for complete search history.

(56) References Cited

U.S. PATENT DOCUMENTS

| 4,093,726 | A | 6/1978 | Winn et al. |
| 6,372,736 | B1 | 4/2002 | Kemp et al. |
| 6,696,437 | B1 * | 2/2004 | Lubisch et al. ......... 514/217.09 |
| 7,462,724 | B2 | 12/2008 | Penning et al. |
| 7,550,603 | B2 | 6/2009 | Zhu et al. |
| 2003/0100582 | A1 | 5/2003 | Sircar et al. |
| 2006/0229351 | A1 | 10/2006 | Zhu et al. |
| 2007/0179136 | A1 | 8/2007 | Penning et al. |
| 2007/0265324 | A1 | 11/2007 | Werner et al. |
| 2009/0030016 | A1 | 1/2009 | Gandhi et al. |
| 2009/0186877 | A1 | 7/2009 | Giranda et al. |

FOREIGN PATENT DOCUMENTS

| DE | 2 248596 | 4/1973 |
| DE | 3830060 A1 | 3/1990 |
| DE | 19916460 A1 | 10/2000 |
| DE | 10021468 A1 | 11/2001 |
| DE | 19920936 A1 | 11/2001 |
| EP | 209 707 | 1/1987 |
| EP | 719 765 | 7/1996 |
| FR | 2 707 011 | 12/1994 |
| GB | 1354554 A | 6/1974 |
| WO | 97/04771 | 2/1997 |
| WO | 97/04771 A1 | 2/1997 |
| WO | 98/39343 A1 | 9/1998 |
| WO | 00/26192 A1 | 5/2000 |
| WO | 00/29384 A1 | 5/2000 |
| WO | 00/32579 A1 | 6/2000 |
| WO | 01/21615 A1 | 3/2001 |
| WO | 01/21634 A1 | 3/2001 |
| WO | 01/82877 A2 | 11/2001 |

OTHER PUBLICATIONS

Golub et al., Science, vol. 286, Oct. 15, 1999, pp. 531-537.*
Gilchrist, et al., "Cyclisation of ortho-Substituted N-Arylbenzimidoyl Nitrenes. Part 2. Preferential Cyclisations at an ortho-Position Bearin a Methoxycarbonyl Group", Journal of Chem. Society, Perkin Transactions 1, GB, Chemical Society, Letchworth, 2303-2307 (1979).
Griffin, et al., "Resistance modifying agents 3. Novel benzimidazole and quinazolinone inhibitors of the DNA repair, enzyme poly(ADP-ribose)polymerase." Pharmaceutical Sciences, 2(1), 43-47 (1996).
Kröger, H., et al., "Synergistic Effects of Thalidomide and Poly(ADP-Ribose) Polymerase Inhibition of Type II Collagen-Induced Arthritis in Mice", Inflammation, 20(2):203-215 (1996).
Burkart, V., et al., "Mice lacking the poly (ADP-ribose) polymerase gene are resistant to pancreatic beta-cell destruction and diabetes development induced by streptozocin", Nat. Med., 5(3):314-319 (1999).
Chen, et al., "Potentiation of the antitumor activity of cisplatin in mice by 3-aminobenzamide and nicotinamide", Cancer Chem. Pham., 22:303-307 (1988).
Cuzzocrea, S., et al., "Protective effects of 3-aminobenzamide, an inhibitor of poly (ADP-ribose) synthase in a carrageenan-induced model of local inflammation", Eur. J. of Pharm., 342:67-76 (1998).
Ehrlich, W., et al., "Inhibition of the induction of collagenase by interleukin-1 in cultured rabbit synovial fibroblasts after treatment with the poly(ADP-ribose)-polymerase inhibitor 3-aminobenzamide", Rheumatol Int., 15:171-172 (1995).

(Continued)

*Primary Examiner*—Laura L. Stockton
(74) *Attorney, Agent, or Firm*—Susan L. Steele; Rachel A. Polster

(57) ABSTRACT

The invention relates to novel 2-phenylbenzimidazoles of general formula (I) or (II), wherein the radicals have the meanings cited in the description, and to their tautomeric forms, possible enantiomeric and diastereomeric forms, to their prodrugs, and to possible physiologically compatible salts. The invention also relates to the production of said compounds and to their use.

20 Claims, No Drawings

OTHER PUBLICATIONS

Szabo, C., et al., "Protection against peroxynitrite-induced fibroblast injury and arthritis development by inhibition of poly(ADP-ribose) synthase", Proc. Natl., Acad. Sci. USA, 95:3867-3872 (1998).

Thiemermann, C., et al., "Inhibition of the activity of poly (ADP ribose) synthhetase reduces ischemia-reperfusion injury in the heart and skeletal muscle", Proc. Natl. Acad. Sci. USA, 94:679-683 (1997).

Weltin, D., et al., "Immunosuppressive Activities of 6(5H)-Phenanthridinone, A New Poly(ADP-Ribose)Polymerase Inhibitor", Int. J. Immunopharmac., 17(4):265-271 (1995).

White, A.W., et al. "Potentiation of cytotoxic drug activity in human tumour cell lines, by amine-substituted 2-arylbenzimidazole-4-carboxamide PARP-1 inhibitor", Bioorganic & Medicinal Chemistry Letters, 2004, 14:2433-2437 (2004).

Co-pending U.S. Appl. No. 11/401,635, filed Apr. 11, 2006.
Co-pending U.S. Appl. No. 12/413,834, filed Mar. 30, 2009.
Co-pending U.S. Appl. No. 11/623,996, filed Jan. 17, 2007.
Co-pending U.S. Appl. No. 11/970,828, filed Jan. 8, 2008.
Co-pending U.S. Appl. No. 12/058,478, filed Mar. 28, 2008.
Co-pending U.S. Appl. No. 12/116,823, filed May 7, 2008.
Co-pending U.S. Appl. No. 12/117,452, filed May 8, 2008.
Co-pending U.S. Appl. No. 12/173,213, filed Jul. 15, 2008.

* cited by examiner

SUBSTITUTED 2-PHENYLBENZIMIDAZOLES, THE PRODUCTION THEREOF AND THEIR USE

This application is a 371 of PCT/EP99/08169 filed Oct. 28, 1999.

The present invention relates to novel 2-phenylbenzimidazoles, their preparation with novel intermediates and their use as inhibitors of the enzyme poly(ADP-ribose) polymerase or PARP (EC 2.4.2.30) for producing drugs.

Poly(ADP-ribose) polymerase (PARP) or, as it is also called, poly(ADP-ribose) synthase (PARS) is a regulatory enzyme found in cell nuclei (K. Ikai et al., *J. Histochem. Cytochem.* 1983, 31, 1261-1264). It is assumed that PARP is involved in the repair of DNA breaks (M. S. Satoh et al., *Nature* 1992, 356, 356-358). Damage or breaks in DNA strands activate the enzyme PARP which, when it is activated, catalyzes the transfer of ADP-ribose from NAD (S. Shaw, *Adv. Radiat. Biol.*, 1984, 11, 1-69). During this, nicotinamide is released from NAD. Nicotinamide is converted back into NAD by other enzymes with consumption of the energy carrier ATP. Overactivation of PARP would accordingly result in a nonphysiologically large consumption of ATP, and this leads in the extreme case to cell damage and cell death.

It is known that free radicals such as superoxided anion, NO and hydrogen peroxide may lead to DNA damage in cells and thus activate PARP. The formation of large amounts of free radicals in observed in a number of pathophysiological states, and it is assumed that this accumulation of free radicals lead or contribute to the observed cell or organ damage. This includes, for example, ischemic states of organs as in stroke, myocardial infarct (C. Thiemermann et al., *Proc. Natl. Acad. Sci. USA* 1997, 94, 679-683) or ischemic of the kidneys but also reperfusion damage as occurs, for example, after lysis of myocardial infarct (see above C. Thiemermann et al.). Inhibition of the enzyme PARP might accordingly be a means of art least partly preventing or moderating this damage. PARP inhibitors might thus represent a novel therapeutic principle for treating a number of diseases.

The enzyme PARP influences the repair of DNA damage and thus might also play a part in the therapy of cancers since a greater action potential on tumor tissue was observed (G. Chen et al. *Cancer Chemo. Pharmacol.* 1988, 22, 303) in combination with substances with cytostatic activity. Nonlimiting examples of tumors are leukemia, glioblastomas, lymphomas, melanomas and carcinomas of the breast and cervix.

In addition, it has been found that PARP inhibitors may show an immunosuppressant effect (D. Weltin et al. *Int. J. Immunopharmacol.* 1995, 17, 265-271).

It has likewise been discovered that PARP is involved in immunological disorders or diseases in which the immune system plays an important part, such as, for example, rheumatoid arthritis and septic shock, and that PARP inhibitors may show a beneficial effect in the course of the disease (H Kröger et al. Inflamation 1996, 20, 203-215; W. Eherlich et al. *Rheumatol. Int.* 1995, 15, 171-172; C. Szabo et al., *Proc. Natl. Acad. Sci. USA* 1998, 95, 3867-3872; S. Cuzzocrea et al. *Eur. J. Pharmacol.* 1998, 342, 67-76)

PARP is understood to include for the purpose of this invention isoenzymes of the PARP enzyme described above. Such isoenzymes are, for example, PARP II and PARP III.

In addition, the PARP inhibitor 3-aminobenzamide showed protective effects in a model of circulatory failure (S. Cuzzocrea et al., *Br. J. Pharmacol.* 1997, 121, 1065-1074).

2-Phenylbenzimidazoles have been described many times. Thus, DE 38 30 060 discloses alkylated derivatives as inhibitors of erythrocyte aggregation. DE 35 22 230 mentions an ester derivative of 2-phenylbenzimidazole as inhibitor of platelet aggregation. Halogen-substituted 2-phenylbenzimidazoles having substituted amine radicals on the phenyl ring have been described in WO 98/06703 as MCP-1-antagonists.

Likewise known are 2-phenylbenzimidazoles in which the benzimidazole group is substituted by an amide group. 5-Amido derivatives of 2-phenylbenzimidazole with alkoxy radicals on the phenyl ring have been described in WO 94/12461 as inhibitors of cAMP phosphodiesterase. It was found in DE 35 46 575 (e.g. Example 15) for analogous derivatives that these compounds induce positive inotropic effects. 4-Amido derivatives having a pyridyl radical in position 3 are likewise mentioned in WO 97/48697 as inhibitors of cAMP phosphodiesterase.

The synthesis of 2-phenylbenzimidazyl-4-amides has been described in J. Chem. Soc. Perkin Trans 1, 1979, 2303-2307. Analogous compounds which have a substituted alkyl chain on the amide residue and are said to have a cytotoxic effect are mentioned in J. Med. Chem. 1990, 33, 814-819. WO 97/04771 mentions benzimidazole-4-amides which inhibit PARS. In particular, derivatives described therein as active have a phenyl ring in position 2, and the phenyl ring may also be substituted by simple substituents such as nitro, methoxy and $CF_3$. Although some of these substances show good inhibition of the enzyme PART, the derivatives described therein have the disadvantage that they show little or no solubility in aqueous solutions and thus cannot be administered as aqueous solution.

In a number of therapies, such as stroke, the active substances are administered intravenously as infusion solution. For this purpose it is necessary to have available substances, in this case PARP inhibitors, which have adequate solubility in water at physiological pH values of close pH values (e.g. pH valued of 5-8), so that an infusion solution can be prepared. Many of the PARP inhibitors described, especially the more effected PARP inhibitors, have the disadvantage, however, that they have only low or no solubility in water at these pH values and thus are unsuitable for intravenous administration. Active substances of this type can be administered only with ancillary substances intended to promote solubility in water (cf. WO 97/04771). These ancillary substances, for example polyethylene glycol and dimethyl sulfoxide, frequently cause side effects or are not tolerated. Very effective PARP inhibitors with adequate solubility in water have not previously been described.

It has been found, surprisingly, that 2-phenyl-benzimidazoles substituted on the phenyl ring by alkoxy radicals and also having an amine residue on the alkoxy side chain are very effective inhibitors but, owing to the incorporation of the aliphatic amine residue, they can form salts with acids and thus show distinctly improved solubility in water.

The present invention describes novel 2-phenylbenzimidazole derivatives of the general formula I which have advantages compared with the previously described compounds and are potent PARP inhibitors and, at the same time, show adequate solubility in water to allow administration as infusion solution.

The present invention relates to substituted 2-phenylbenzimidazoles of the general formula I or II

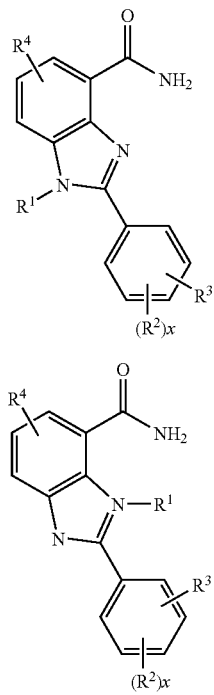

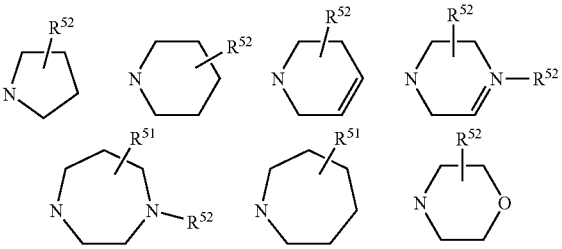

p may be 0 or 1 and
q may be 0 or 1, and
r may be 0 or 1 and
s may be 0 or 1 and
u may be 0 or 1 and
v may be 0 or 1
G may be $NR^{51}R^{52}$ or and $R^{51}$ is hydrogen or branched and unbranched $C_1$-$C_6$-alkyl, $(CH_2)_t$—K and $R^{52}$ is hydrogen, branched and unbranched $C_1$-$C_6$-alkyl, phenyl,

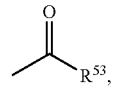

—$SO_2R^{53}$, —(C=N)—$R^{53}$, —CO—$NHR^{53}$, —(C=N)—$NHR^{53}$, in which $R^{53}$ may be branched or unbranched O—$C_1$-$C_6$-alkyl, phenyl, branched or unbranched $C_1$-$C_4$-alkylphenyl, where in the case of $R^{52}$ and $R^{53}$ independently of one another one hydrogen of the $C_1$-$C_6$-alkyl radical may be substituted by one of the following radicals: OH, O—$C_1$-$C_4$-alkyl, cyclohexyl, cyclopentyl, tetrahydronaphthyl, cyclopropyl, cyclobutyl, cycloheptyl, naphthyl and phenyl, it also being possible for the carbocycles of the radicals $R^{52}$ and $R^{53}$ independently of one another to carry one or two of the following radicals: branched or unbranched $C_1$-$C_6$-alkyl, branched or unbranched O—$C_1$-$C_4$-alkyl, OH, F, Cl, Br, I, $CF_3$, $NO_2$, $NH_2$, CN, COOH, COO$C_1$-$C_4$-alkyl, $C_1$-$C_4$-alkylamino, $CCl_3$, $C_1$-$C_4$-dialkylamino, $SO_2$—$C_1$-$C_4$-alkyl, $SO_2$phenyl, $CONH_2$, CONH—$C_1$-$C_4$-alkyl, CONHphenyl, CONH—$C_1$-$C_4$-alkylphenyl, $NHSO_2$—$C_1$-$C_4$-alkyl, $NHSO_2$phenyl, S—$C_1$-$C_4$-alkyl,

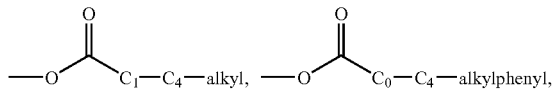

CHO, $CH_2$—O—$C_1$-$C_4$-alkyl, —$CH_2$O—$C_1$-$C_4$-alkylphenyl, —$CH_2$OH, —SO—$C_1$-$C_4$-alkyl, —SO—$C_1$-$C_4$-alkylphenyl, —$SO_2NH_2$, —$SO_2NH$—$C_1$-$C_4$-alkyl and two radicals form a bridge —O—$(CH_2)_{1,2}$—O—, in which $R^1$ is hydrogen, branched and unbranched $C_1$-$C_6$-alkyl, it also being possible for one C atom of the alkyl radical to carry $OR^{11}$ or a group $R^5$, where
$R^{11}$ is hydrogen or $C_1$-$C_4$-alkyl, and $R^2$ is hydrogen, chlorine, bromine, iodine, fluorine, $CF_3$, nitro, $NHCOR^{21}$, $NR^{22}R^{23}$, OH, O—$C_1$-$C_4$-alkyl, O—$C_1$-$C_4$-alkylphenyl, $NH_2$, phenyl, it also being possible for the phenyl rings to be substituted by at most two radicals $R^{24}$, and $R^{21}$ and $R^{22}$ independently of one another are hydrogen or $C_1$-$C_4$-alkyl and $R^{23}$ is hydrogen, $C_1$-$C_4$-alkyl or phenyl, and $R^{24}$ is OH, $C_1$-$C_6$-alkyl, O—$C_1$-$C_4$-alkyl, chlorine, bromine, iodine, fluorine, $CF_3$, nitro, $NH_2$, and x may be 0, 1 or 2 and $R^3$ is -D-$(F^1)_p$-$(E)_q$-$(F^2)_r$-G, where p, q and r may not simultaneously be 0, or is -E-$(D)_u$-$(F^2)_s$-$(G)_v$, it also being possible for the radical E to be substituted by one or two radicals A, or $R^3$ is B and $R^4$ is hydrogen, chlorine, fluorine, bromine, iodine, branched and unbranched $C_1$-$C_6$-alkyl, OH, nitro, $CF_3$, CN, $NR^{41}R^{42}$, NH—CO—$R^{43}$, O—$C_1$-$C_4$-alkyl, where
$R^{41}$ and $R^{42}$ independently of one another are hydrogen or $C_1$-$C_4$-alkyl and
$R^{43}$ is hydrogen, $C_1$-$C_4$-alkyl, $C_1$-$C_4$-alkylphenyl or phenyl, and D is S or O, E is phenyl, imidazole, pyrrole, thiophene, pyridine, pyrimidine, piperazine, pyrazine, furan, thiazole, isoxazole, pyrrolidine, piperidine, trihydroazepine and $F^1$ is a chain of 1 to 8 carbon atoms, it also being possible for one carbon atom of the chain to carry an OH or O—$C_1$-$C_4$-alkyl group and $F^2$ is a chain of 1 to 8 carbon atoms, it also being possible for one carbon atom of the chain to carry an OH or O—$C_1$-$C_4$-alkyl group and B may be

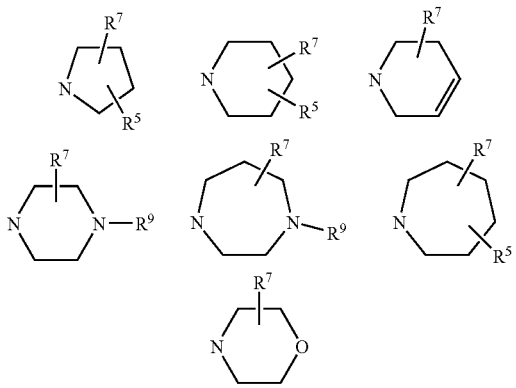

and

A may be hydrogen, chlorine, bromine, iodine, fluorine, $CF_3$, nitro, OH, O—$C_1$-$C_4$-alkyl, O—$C_1$-$C_4$-alkylphenyl, $NH_2$, branched and unbranched CN, NH—CO—$R^{33}$, where $R^{33}$ is hydrogen, $C_1$-$C_4$-alkyl or phenyl and t is 0, 1, 2, 3, 4 and K is phenyl which may carry at most two radicals R, is $NR^{k1}R^{k2}$ (where $R^{k1}$ and $R^{k2}$ are as defined for $R^{41}$ and $R^{42}$ respectively), NH—$C_1$-$C_4$-alkylphenyl, pyrrolidine, piperidine, 1,2,5,6-tetrahydropyridine, morpholine, trihydroazepine, piperazine, which may also be substituted by an alkyl radical $C_1$-$C_6$-alkyl, and homopiperazine, which may also be substituted by an alkyl radical $C_1$-$C_6$-alkyl, and $R^5$ may be hydrogen, $C_1$-$C_6$-alkyl, $NR^7R^9$ and

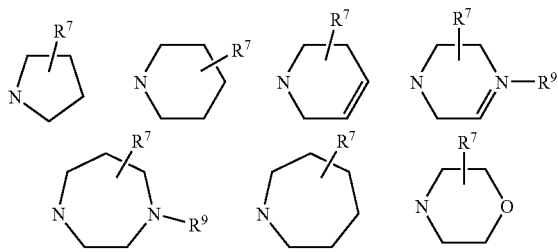

and $R^7$ is hydrogen, $C_1$-$C_6$-alkyl, $C_1$-$C_4$-alkylphenyl, phenyl, it also being possible for the rings to be substituted by up to two radicals $R^{71}$, and $R^{71}$ is OH, $C_1$-$C_6$-alkyl, O—$C_1$-$C_4$-alkyl, chlorine, bromine, iodine, fluorine, $CF_3$, nitro, $NH_2$, and $R^8$ is hydrogen, $C_1$-$C_6$-alkyl, phenyl, $C_1$-$C_4$-alkylphenyl, it also being possible for the ring to be substituted by up to two radicals $R^{81}$, and $R^{81}$ is OH, $C_1$-$C_6$-alkyl, O—$C_1$-$C_4$-alkyl, chlorine, bromine, iodine, fluorine, $CF_3$, nitro, $NH_2$, and $R^9$ is hydrogen, $COCH_3$, CO—O—$C_1$-$C_4$-alkyl, $COCF_3$, branched and unbranched, $C_1$-$C_6$-alkyl, it being possible for one or two hydrogens of the $C_1$-$C_6$-alkyl radical to be substituted in each case by one of the following radicals: OH, O—$C_1$-$C_4$-alkyl and phenyl, and for the phenyl ring also to carry one or two of the following radicals: iodine, chlorine, bromine, flourine, branched or unbranched $C_1$-$C_6$-alkyl, nitro, amino, $C_1$-$C_4$-alkylamino, $C_1$-$C_4$-dialkylamino, OH, CN, $CF_3$, $SO_2$—$C_1$-$C_4$-alkyl, and and the tautomeric forms, possible enantiomeric and diastereomeric forms thereof, the prodrugs thereof and pharmacologically tolerated salts.

Preference is given to compounds in which the radicals are as defined below:

$R^1$ is hydrogen, branched and unbranched $C_1$-$C_6$-alkyl, it also being possible for one C atom of the alkyl radical to carry $OR^{11}$ or a group $R^5$, where $R^{11}$ is hydrogen or $C_1$-$C_4$-alkyl, and $R^2$ is hydrogen, chlorine, fluorine, bromine, iodine, branched and unbranched $C_1$-$C_6$-alkyl, nitro, $CF_3$, CN, $NR^{21}R^{22}$, NH—CO—$R^{23}$, $OR^{21}$, where $R^{21}$ and $R^{22}$ are, independently of one another, hydrogen or $C_1$-$C_4$-alkyl, and $R^{23}$ are hydrogen, $C_1$-$C_4$-alkyl or phenyl, and $R^3$ is —O—$(CH_2)_o$—$(CHR^{31})_m$—$(CH_2)_n$—$R^5$, where $R^{31}$ is hydrogen, $C_1$-$C_4$-alkyl, OH and O—$C_1$-$C_4$-alkyl, m, o is, independently of one another, 0, 1 or 2, and n is 1, 2, 3 or 4, and $R^4$ is hydrogen, branched and unbranched $C_1$-$C_6$-alkyl, chlorine, bromine, fluorine, nitro, cyano, $NR^{41}R^{42}$, NH—CO—$R^{43}$, $OR^{41}$, where $R^{41}$ and $R^{42}$ are, independently of one another, hydrogen or $C_1$-$C_4$-alkyl, and $R^{43}$ are $C_1$-$C_4$-alkyl or phenyl, and $R^5$ is $NR^{51}R^{52}$ or one of the following radicals

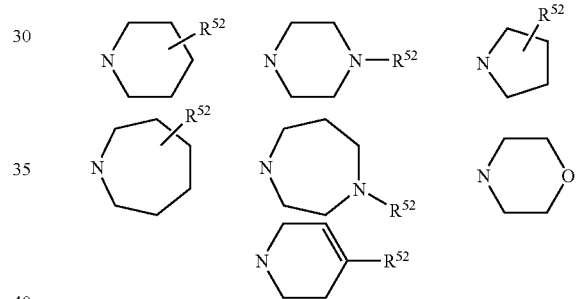

where $R^{51}$ is hydrogen and branched and unbranched $C_1$-$C_6$-alkyl, and $R^{52}$ is hydrogen, branched and unbranched $C_1$-$C_6$-alkyl, phenyl,

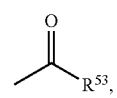

—$SO_2R^{53}$, in which $R^{53}$ is branched or unbranched O—$C_1$-$C_6$-alkyl, phenyl, branched or unbranched $C_1$-$C_4$-alkyl-phenyl, where one hydrogen in the $C_1$-$C_6$-alkyl radical in $R^{52}$ and $R^{53}$ can, independently of one another, be substituted by one of the following radicals: OH, O—$C_1$-$C_4$-alkyl, cyclohexyl, cyclopentyl, tetrahydronaphthyl, cyclopropyl, cyclobutyl, cycloheptyl, naphthyl and phenyl, where the carbocycles of the $R^{52}$ and $R^{53}$ radicals may also, independently of one another, carry one or two of the following radicals: branched or unbranched $C_1$-$C_6$-alkyl, branched or unbranched O—$C_1$-$C_4$-alkyl, OH, F, Cl, Br, I, $CF_3$, $NO_2$, $NH_2$, CN, COOH, $COOC_1$-$C_4$- alkyl, $C_1$-$C_4$-alkylamino, $CCl_3$, $C_1$-$C_4$-dialkylamino, $SO_2$—$C_1$-$C_4$-alkyl, $SO_2$-phenyl, $CONH_2$, CONH—$C_1$-$C_4$-alkyl, CONHphenyl, CONH—$C_1$-$C_4$-alkyl-phenyl, $NHSO_2$—$C_1$-$C_4$-alkyl, $NHSO_2$-phenyl, S—$C_1$-$C_4$-alkyl,

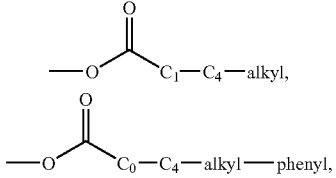

CHO, $CH_2$—O—$C_1$-$C_4$-alkyl, —$CH_2$O—$C_1$-$C_4$-alkyl-phenyl, —$CH_2$OH, —SO—$C_1$-$C_4$-alkyl, —SO—$C_1$-$C_4$-alkyl-phenyl, $SO_2NH_2$, —$SO_2NH$—$C_1$-$C_4$-alkyl and two radicals form a bridge —O—$(CH_2)_{1,2}$—O—.

Particularly preferred positions for the $R^2$ radical in the general formula I or II are position 3 and position 4 relative to the benzimidazole ring. Position 3 or position 4 relative to the benzimidazole ring is likewise preferred for the $R^3$ radical.

The particularly preferred meaning of $R^1$ is hydrogen.

The particularly preferred meaning of $R^2$ is hydrogen, branched or unbranched $C_1$-$C_6$-alkyl, nitro, CN, $NH_2$, O—$C_1$-$C_4$-alkyl.

The particularly preferred meaning of $R^3$ is —O—$(CH_2)_p$—$R^5$ with p equal to 2, 3 or 4.

$R^5$ is preferably a 6-membered ring, in particular piperazine, $R^{52}$ is preferably an optionally substituted phenyl ring, especially if $R^5$ is a 6-membered ring.

The particularly preferred meaning of $R^4$ is hydrogen.

The respective combinations of the above preferred meanings are very particularly preferred.

Preference is also given to compounds where the substituents are as defined below:

$R^1$ is hydrogen, branched and unbranched $C_1$-$C_6$-alkyl, it also being possible for one C atom of the alkyl radical to carry $OR^{11}$ or a group $R^5$, where $R^{11}$ is hydrogen or $C_1$-$C_4$-alkyl, and $R^2$ is hydrogen, chlorine, fluorine, bromine, iodine, branched and unbranched, $C_1$-$C_6$-alkyl nitro, $CF_3$, CN, $NR^{21}R^{22}$, NH—CO—$R^{23}$, $OR^{21}$, where $R^{21}$ and $R^{22}$ independently of one another are hydrogen or $C_1$-$C_4$-alkyl and $R^{23}$ is hydrogen, $C_1$-$C_4$-alkyl or phenyl, and $R^3$ is

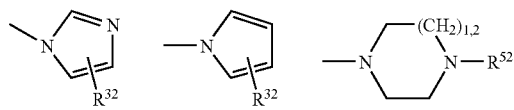

and $R^{32}$ is hydrogen, CHO or $(CH_2)_o$—$CHR^{31})_m$—$CH_2)_n$-G or $(CH_2)_p$-G where $R^{31}$ is hydrogen, $C_1$-$C_4$-alkyl, OH and O—$C_1$-$C_4$-alkyl, m, o independently of one another are 0, 1 or 2 and n is 1, 2, 3 or 4, and $R^4$ is hydrogen, branched and unbranched $C_1$-$C_6$-alkyl, chlorine, bromine, fluorine, nitro, cyano, $NR^{41}R^{42}$, NH—CO—$R^{43}$, $OR^{41}$, where $R^{41}$ and $R^{42}$ independently of one another are hydrogen or $C_1$-$C_4$-alkyl and $R^{43}$ is $C_1$-$C_4$-alkyl or phenyl, and $R^5$ is $NR^{51}R^{52}$ or one of the radicals below where $R^{51}$ is hydrogen and branched and unbranched $C_1$-$C_6$-alkyl and $R^{52}$ is hydrogen, $COCH_3$, CO—O—$C_1$-$C_4$-alkyl, $COCF_3$, branched and unbranched $C_1$-$C_6$-alkyl, it being possible for one hydrogen of the $C_1$-$C_6$-alkyl radical to be substituted by one of the following radicals: OH, O—$C_1$-$C_4$-alkyl and phenyl and for the phenyl ring also to carry one or two of the following radicals:

chlorine, bromine, fluorine, branched and unbranched $C_1$-$C_4$-alkyl, nitro, amino, $C_1$-$C_4$-alkylamino, $C_1$-$C_4$-dialkylamino, OH, O—$C_1$-$C_4$-alkyl, CN, $SO_2$—$C_1$-$C_4$-alkyl.

Particularly preferred positions for the radical $R^2$ in the formula I or II are the 3-position and the 4-position with respect to the benzimidazole ring. For the radical $R^3$, preference is likewise given to the 3-position or 4-position with respect to the benzimidazole ring.

The particularly preferred meaning of $R^1$ is hydrogen.

The particularly preferred meaning of $R^2$ is hydrogen, branched or unbranched $C_1$-$C_6$-alkyl, nitro, CN, $NH_2$, O—$C_1$-$C_4$-alkyl. Particularly preferably, $R^2$ is hydrogen.

For $R^3$ being the particularly preferred meaning of $R^{31}$ is hydrogen or —$(CH_2)_p$—$R^5$, where p is 1 or 2 and $R^{52}$ may be hydrogen, branched and unbranched $C_1$-$C_6$-alkyl, where one hydrogen of the $C_1$-$C_6$-alkyl radical may be substituted by one of the following radicals: OH, O—$C_1$-$C_4$-alkyl and phenyl, and where the phenyl ring may also carry one or two of the following radicals: chlorine, bromine, fluorine, branched and unbranched $C_1$-$C_4$-alkyl, nitro, amino, $C_1$-$C_4$-alkylamino, $C_1$-$C_4$-dialkylamino, OH, O—$C_1$-$C_4$-alkyl, CN, $SO_2$—$C_1$-$C_4$-alkyl.

For $R^3$ being the particularly preferred meaning of $R^{31}$ is hydrogen or —$(CH_2)_p$—$R^5$, where p is 1 or 2 and $R^{52}$ may be hydrogen, branched and unbranched $C_1$-$C_6$-alkyl, where one hydrogen of the $C_1$-$C_6$-alkyl radical may be substituted by one of the following radicals: OH, O—$C_1$-$C_4$-alkyl and phenyl, and where the phenyl ring may also carry one or two of the following radicals: chlorine, bromine, fluorine, branched and unbranched $C_1$-$C_4$-alkyl, nitro, amino, $C_1$-$C_4$-alkylamino, $C_1$-$C_4$-dialkylamino, OH, O—$C_1$-$C_4$-alkyl, CN, $SO_2$—$C_1$-$C_4$-alkyl.

For $R^3$ being the particularly preferred meaning of $R^{52}$ can be hydrogen, branched and unbranched $C_1$-$C_6$-alkyl, where one hydrogen of the $C_1$-$C_6$-alkyl radical may be substituted by one of the following radicals: OH, O—$C_1$-$C_4$-alkyl and phenyl, and where the phenyl ring may also carry one or two of the following radicals:

chlorine, bromine, fluorine, branched and unbranched $C_1$-$C_4$-alkyl, nitro, amino, $C_1$-$C_4$-alkylamino, $C_1$-$C_4$-dialkylamino, OH, O—$C_1$-$C_4$-alkyl, CN, $SO_2$—$C_1$-$C_4$-alkyl.

The particularly preferred meaning of $R^4$ is hydrogen.

Very particular preference is given to the respective combinations of the preferred meanings above.

The compounds of the formula I can be employed as racemates, as enantiomerically pure compounds or as diastereomers. If enantiomerically pure compounds are required, these can be obtained, for example, by carrying out a classical racemate resolution with the compounds of the formula I or their intermediates using a suitable optically active base or acid.

The invention also relates to compounds which are mesomeric or tautomeric to compounds of the formula I.

The invention further relates to the physiologically tolerated salts of the compounds I which can be obtained by reacting compounds I with a suitable acid or base. Suitable acids and bases are listed, for example, in Fortschritte der Arzneimittelforschung, 1966, Birkhäuser Verlag, Volume 10, pp. 224-285. These include, for example, hydrochloric acid, citric acid, tartaric acid, lactic acid, phosphoric acid, methanesulfonic acid, acetic acid, formic acid, maleic acid, fumaric acid etc., or sodium hydroxide, lithium hydroxide, potassium hydroxide and tris.

Prodrugs mean compounds which are metabolized in vivo to compounds of the general formula I or II. Typical prodrugs are phosphates, carbamates of amino acids, esters and others.

The 2-phenylbenzimidazoles of the formula I or II according to the invention can be prepared in various ways which are outlined in the following synthesis schemes.

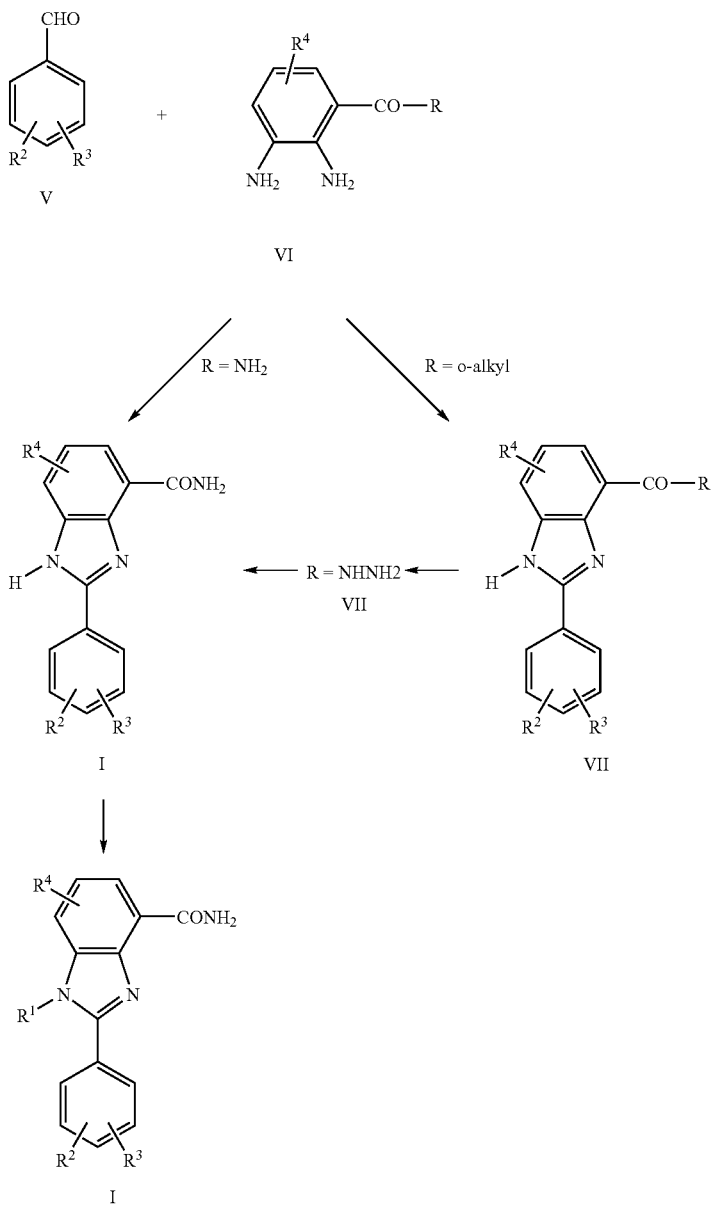

Synthesis scheme 1

Condensation of benzaldehydes V with phenylenediamines VI results in the benzimidazole VII, preferably using polar solvents such as ethanol or dimethylformamide and adding acids such as acetic acid, at elevated temperature, usually 80 to 120° C. It is beneficial for the reaction to add weak oxidizing agents such as copper(II) salts, which are added as aqueous solution.

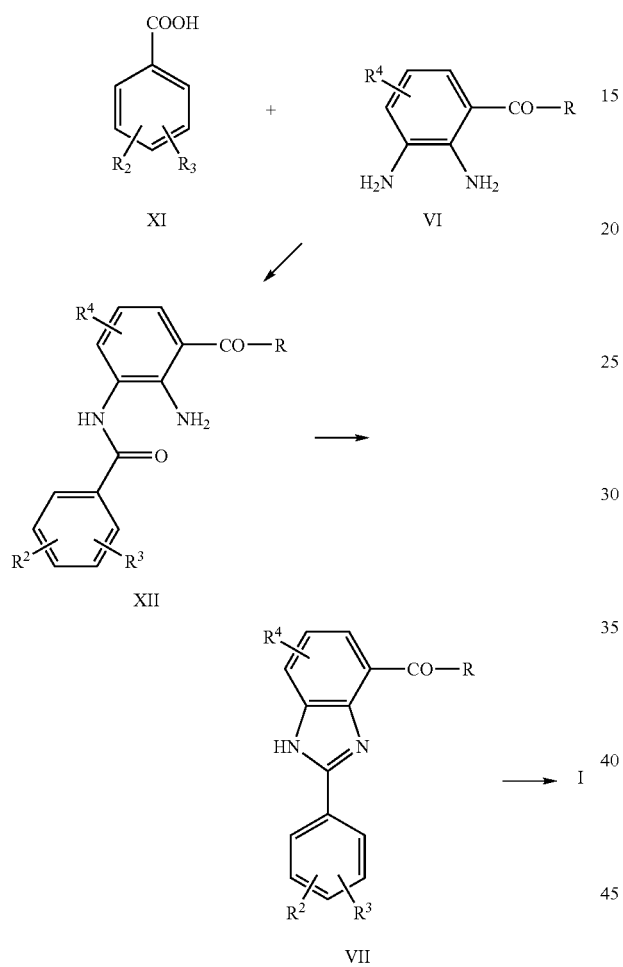

Synthesis scheme 2

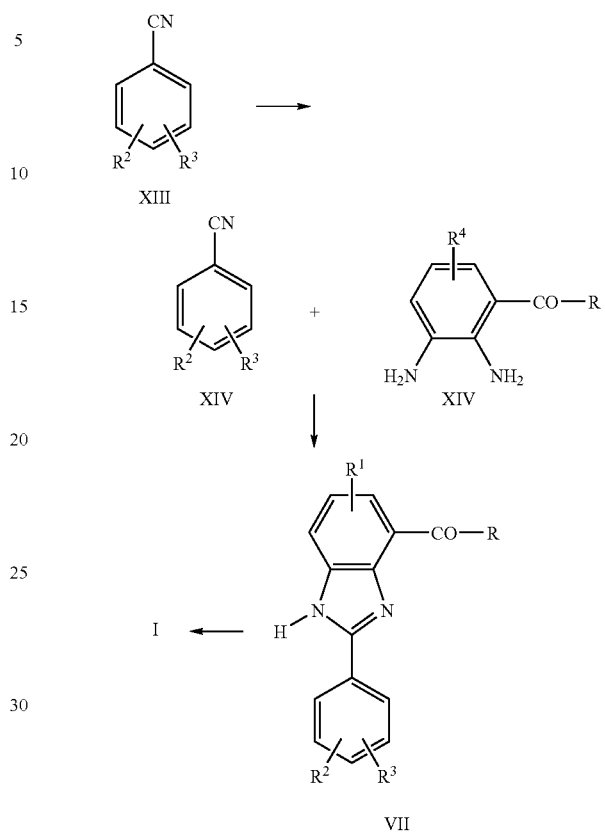

Synthesis scheme 3

When R=NH$_2$ in the phenylenediamine VI, the condensation directly results in compounds I according to the invention. Otherwise, it is possible, if R is O-alkyl, to react this ester with ammonia, optionally at elevated temperature and elevated pressure, to give the amide I. Alternatively, the ester XII can be reacted with hydrazine in polar solvents such as the alcohols butanol and ethanol, or else dimethylformamide, at elevated temperatures, preferably 80 to 130° C., resulting in a hydrazide XII (R=NHNH$_2$) which can then be reduced under reductive conditions, such as with raney nickels in alcohols under reflux, to the amide I.

Introduction of the R1 radical on the benzimidazole residue in I (R$_1$=H) takes place under customary alkylation conditions as it for example in J. Het. Chem. 1995, 32, 707f and in Tetrahedron 1994, 50, 5535), although it is necessary to employ the reactant R$_1$-L (L=leaving group Cl, Br and I).

As an alternative to the benzaldehydes V shown in scheme 1, it is also possible to employ benzoic acids such as XI (see scheme 2) or benzonitriles such as XIII (see scheme 3) in place of the benzaldehyde. The preparation of these derivatives is analogous to the preparation of the substituted benzaldehydes V. Starting from XI, the condensation to VII takes place in two stages. Firstly, the benzoic acid XI is reacted with the aniline VI in a peptide-like coupling to give the amide XII. Conventional Houben-Weyl, Methoden der Ogranischen Chemie, 4th Ed. E5, chapter V, or C. R. Larock, Comprehensive Organic Transformations, VCH Publisher, 1989, page 972 et seq. The ring closure takes place to the benzimidazole then takes place at elevated temperature, for example 60 to 180° C., with or without solvent such as dimethylformamide, with the addition of acids such as acetic acid, or directly in acetic acid itself.

Reaction of the phenylenediamine VI with ah benzonitrile XIII likewise takes place under conventional conditions. This can be carried out in solvents such as dimethylformamide with the addition of acids at elevated temperatures such as 60 to 200° C. However, it is also possible to use the conventional methods for preparing amidines from benzonitriles, as described in Houben-Weyl, Methoden der Ogranischen Chemie, E5, p. 1304 f., *J. Amer. Chem. Soc.* 1957, 427 and *J. Org. Chem.* 1987, 1017.

The present invention also relates to 2,3-diaminobenzamides of the formula XX, XXI and their synthesis and use as intermediates.

Diaminobenzamides carrying a substituted alkyl chain on the amide radical are disclosed in WO 9631462 for the treatment of neurodegenerative disorders. Diaminobenzamides carrying a substituted aryl radical on the amide radical are disclosed in JP 09059236 for the treatment of inflammations and allergies. The effects of benzohydroxamic acids on DNA synthesis were investigated in *Bull. Soc. Chim. Belg.* 1997, 106, 767.

Aminodibenzodiazepinones were prepared in P. V. Khadikar et al., *J. Heterocycl. Chem.* 1998, 35, 675. The synthesis of 2-phenylbenzimidazyl-4-amides has been described in *J. Chem. Soc. Perkin Trans* 1, 1979, 2302-2307. Analogous compounds, which additionally carry a substituted alkyl chain on the amide radical, and which are said to have cytotoxic action, are listed in *J. Med. Chem.* 1990, 33, 814-819. WO 97/04771 lists benzimidazole-4-amides which inhibit the enzyme PARP. In particular, derivatives carrying a phenyl ring in the 2-position, where the phenyl ring may additionally be substituted by simple substituents, such as nitro, methoxy and $CF_3$, have been described as active.

To demonstrate the synthesis strategy in WO 97/04771, Scheme 4 shows the synthesis of 2-phenylbenzimidazole-4-carboxamide (NU 1070) in an exemplary manner.

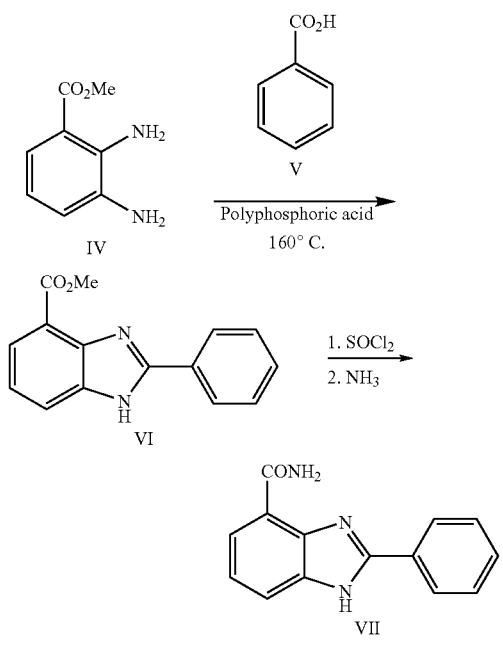

The reaction of methyl diaminobenzoate IV with benzoic acid V in polyphosphoric acid gives the benzimidazole-4-carboxylate VI in 20% yield. Ester VI is subsequently converted into the amide VII via formation of the acyl chloride. For this step, the authors report a yield of 62%. The resulting overall yield for the synthesis sequence is 12%. The overall yields for the syntheses of all the other examples mentioned in WO 97/04771 are within the range of 5 to 19%. A great disadvantage of this synthesis strategy is the fact that each compound which is analogous to VI requires subsequent conversion into the amide, only the amide being the active PARP inhibitor.

The present invention provides 2,3-diaminobenzamides of the formulae XX and XXI:

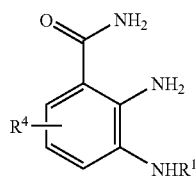

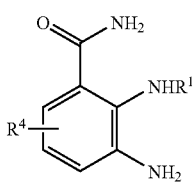

in which
$R^4$ and $R^1$ are as defined above, and salts thereof.

The compounds XX or XXI are synthesized in accordance with Scheme 5, by hydrazinolysis of a suitably substituted ester VIII with hydrazine hydrate in an alcohol such as n-butanol at 100° C. and subsequent reduction of the hydrazide with Raney nickel in polar solvents, such as dimethylformamide, at 100° C.

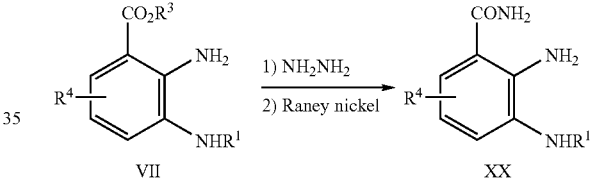

Surprisingly, the syntheses of benzimidazole-4-amides from compounds XX or XXI moreover resulted in higher overall yields than the syntheses described in WO 97/04771.

The synthesis of benzimidazole-4-amides from the compounds of the formulae XX and XXI is described in Scheme 6 and Scheme 7, respectively.

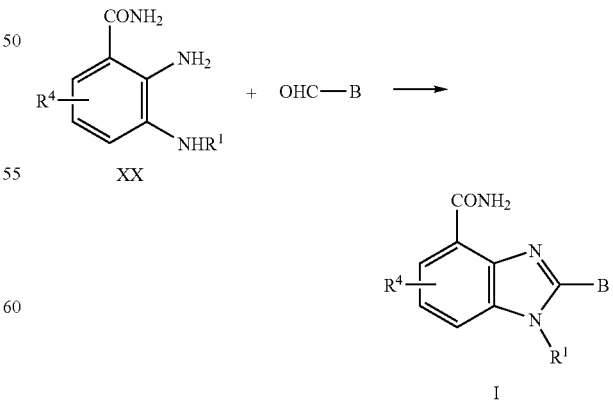

Condensation of a suitable aldehyde OHC—B with compounds XX or XXI gives the benzimidazole I, the reaction preferably being carried out in polar solvents, such as ethanol or dimethylformamide, with addition of acids, such as acetic acid, at elevated temperature, usually from 80 to 120° C. The addition of weak oxidizing agents, such as copper(II) salts, which are added as aqueous solution, has a favorable effect on the reaction.

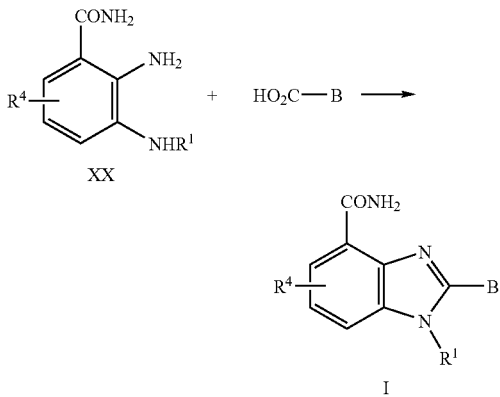

Scheme 7

Using suitable acids HOOC—B, initially a peptide-like coupling with the compounds XX or XXI is effected. Here, the customary conditions, listed, for example, in Houben Weyl, Methoden der Organischen Chemie, 4th Ed, E5, Chap. V or C. R. Larock, Comprehensive Organic Transformations, VCH Publisher, 1989, p. 972f, are employed. Ring closure is then effected at elevated temperature, for example at from 60 to 180° C., in the presence or absence of solvents such as dimethylformamide, with addition of acids such as acetic acid, or directly in acetic acid.

To compare the overall yields of the novel synthesis strategy with those in WO 97/04771, the synthesis of 2-phenylbenzimidazole-4-carboxamide is shown in Scheme 11. The reaction of ester XIV to give amide XV proceeds with a yield of 70%. The synthesis of the benzimidazole VII by condensation of XV with benzaldehyde XVI, followed by oxidation, takes place with a yield of 85%. The resulting overall yield of 60% exceeds the corresponding overall yield of 12% in WO 97/04771.

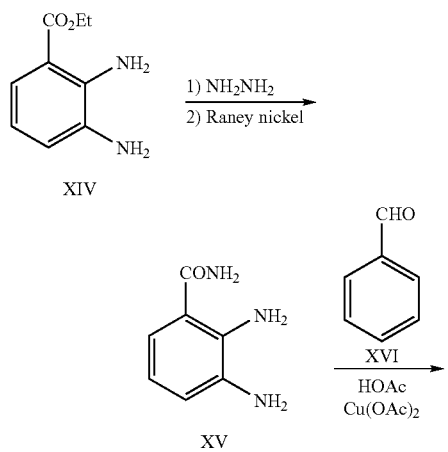

Scheme 8

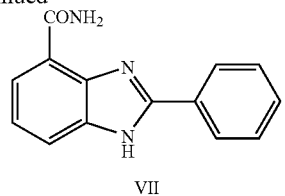

VII

The substituted 2-phenylbenzimidazoles I or II comprised in the present invention are inhibitors of the enzyme poly (ADP-ribose) polymerase or PARP (EC 2.4.2.30).

The inhibitory effect of the substituted 2-phenylbenzimidazoles I or II was determined using an enzyme assay disclosed in the literature, with a $K_i$ being determined as gage of the effect. The 2-phenylbenzimidazoles I were measured in this way for an inhibitory effect on the enzyme poly(ADP-ribose) polymerase or PARP (EC 2.4.2.30).

There is a great need for PARP inhibitors with high inhibitory potential ($K_i$<50 nm) and good bioavailability. A precondition for identifying such compounds and optimizing them is a rapid and efficient assay system for quantifying the activity of poly(ADP-ribose) polymerase. All assay systems available to date are based on the use of radioactive NAD as substrate for PARP and quantification of the radioactivity incorporated into the poly(ADP-ribose) polymer. Thus, PARP assays using [$^{14}$C]NAD are described in JBC 254:9, 3647-3651, 1979; Biochemical Pharmacology 44:5, 947-953, 1992; Analytical Biochemistry 195, 227, 1-13, 1995; JBC 267:3, 1569-1575, or using [$\alpha^{32}$P]NAD are described in Analytical Biochemistry 195, 226-231, 1991; JBC 264:8, 4312-4317, 1989; Anti-Cancer Drug Design 10, 507-514, 1995, or using [$^3$H]NAD are described in JBC 253:18, 6459, 6466, 1978; Eur J Biochem, 102, 43-57, 1979; J Clinical Investigation 77, 1312-1320, 1986.

These methods are both elaborate, with limited throughput, and problematical in environmental and operational safety terms because of the radioactivity used. There is thus a great need for rapid, nonradioactive assay systems.

The invention further relates to an in vitro detection method, which can be carried out homogeneously or heterogeneously, for PARP inhibitors, which comprises
a) incubating an unsupported or supported polyADP-ribosylatable target with a reaction mixture comprising
 a1) a PARP;
 a2) a PARP activator; and
 a3) a PARP inhibitor or an analyte in which at least one PARP inhibitor is suspected;
b) carrying out the polyADP-ribosylation reaction; and
c) determining the polyADP-ribosylation of the target qualitatively or quantitatively using an anti-poly(ADP-ribose) antibody.

The detection method is preferably carried out by preincubating the PARP homolog with the PARP activator and the PARP inhibitor or an analyte in which at least one PARP inhibitor is suspected, for example for about 1-30 minutes, before carrying out the polyADP ribosylation reaction.

After activation by DNA with single strand breaks (referred to as "activated DNA" according to the invention), PARP polyADP-ribosylates a large number of nuclear proteins in the presence of NAD. These proteins include, on the one hand, PARP itself, but also histones etc.

The polyADP-ribosylatable table preferably used in the detection method is a histone protein in its native form or a polyADP-ribosylatable equivalent derived therefrom. A histone preparation supplied by Sigma (SIGMA catalog No. H-7755; histone type II as from calf thymus, Luck J M et al., J. Biol. Chem., 235, 2801 (1960)) was used by way of example. It is possible in principle to use all types of proteins or parts thereof amenable to polyADP-ribosylation of PARP. These are preferably nuclear proteins, e.g. histone, DNA-polymerase, telomerase or PARP itself. Synthetic peptides derived from the corresponding proteins can also act as target.

In the ELISA assay it is possible to use amounts of histones in the range from 0.1 μm/well to 100 μm/well, preferably 1 μm/well to 10 μm/well. The amounts of the PARP enzyme are in the range from 0.2 pmol/well to 2 nmol/well, preferably from 2 pmol/well to 200 pmol/well; the reaction mixture in each comprising 100 μl/well. Reductions to smaller wells and correspondingly smaller reaction volumes are possible. In the HTRF assay, identical amounts of PART are employed, and the amount of histone or modified histones is in the range from 2 ng/well to 25 μg/well, preferably 25 ng/well to 2.5 μg/well, the reaction mixture in each case comprising 50 μl/well. Reduction to smaller wells and correspondingly smaller reaction volumes are possible.

The PARP activator used according to the invention is preferably activated DNA.

Various types of damaged DNA can function as activators. DNA damage can be produced by digestion with DNAases or other DNA-modifying enzymes (e.g. restriction endocucleases), by irradiation or other physical method or chemical treatment of the DNA. It is further possible to simulate the DNA damage situation in a targeted manner by using synthetic oligonucleotides. In the assays indicated by way of example, activated DNA from calf thymus was employed (SIGMA, Product No. D4522, CAS: 91080-16-9, prepared by the method of Aposhian and Kornberg using calf thymus DNA (SIGMA D-1501) and deoxyribonuclease type I (D-4263). Aposhian HV and Kornberg A., J. Biol. Chem., 237, 519 (1962)). The activated DAN was used in a concentration range of 0.1-1000 μg/ml, preferably from 1 to 100 μg/ml, in the reaction step.

The polyADP ribosylation reaction is started in the method according to the invention by adding $NAD^+$.

The NAD concentrations were in a range from 0.1 μM to 10 mM, preferably from 10 μM to 1 mM.

In the variant of the above method which can be carried out heterogeneously, the polyADP ribosylation of the supported target is determined using anti-poly(ADP-ribose) antibodies. To do this, the reaction mixture is separated from the supported target, washed and incubated with the antibody. This antibody can itself be labeled. However, it is preferable to use for detecting bound anti-poly(ADP-ribose) antibody a labeled secondary antibody or a corresponding labeled antibody fragment. Suitable labels are, for example, radiolabeling, chromophore- or fluorophore-labeling, biotinylation, chemiluminescence labeling, labeling with paramagnetic metal or, in particular, enzyme labels, e.g. with horseradish peroxidase. Appropriate detection techniques are generally known to the skilled worker.

In the variant of the above process which can be carried out homogeneously, the unsupported target is labeled with an acceptor fluorophore. The target preferably used in this case is biotinylated histone, the acceptor fluorophore being coupled via avidin or streptavidin to the biotin groups of the histone. Particularly suitable as acceptor fluorophore are phycobiliproteins (e.g. phycocyanins, phycoerythrins), e.g. R-phycocyanin (R—PC), allophycocyanin (APC), R-phycoerythrin (R-PE), C-phycocyanin (C—PC), B-phycoerythrin (B-PE) or their combinations with one another or with fluorescent dyes such as Cy5, Cy7 or Texas Red (tandem system).

(Thammapalerd N. et al., Southeast Asian Journal of Tropical Medicine & Public Health. 27(2):297-303, 1996; Kronick M. N. et al. Clinical Chemistry. 29(9):1582-6, 1983; Hicks J. M., Human Pathology. 15 (2):112-6, 1984). The dye XL665 used in this is a crosslinked allophycocyanin (Glazer A N, Rev. Microbiol. 36:173 198 (1982); Kronick M. N., J. Imm. Meth. 92:1 13 (1986); MacColl R. et al., Phycobiliproteins, CRC Press, Inc., Boca Raton, Fla. (1987); MacColl R. et al., Arch. Biochem. Biophys. 208:1:42 48 (1981)).

It is additionally preferred in the homogeneous method to determine the polyADP ribosylation of the unsupported target using anti-poly(ADP-ribose) antibody which is labeled with a donor fluorophore which is able to transfer energy to the acceptor fluorophore when donor and acceptor are close in space owing to binding of the labeled antibody to the polyADP-ribosylated histone. A europium cryptate is preferably used as donor fluorophore for the anti-poly(ADP-ribose) antibody.

Besides the europium cryptate used, other compounds are also possible as potential donor molecules. This may entail, on the one hand, modification of the cryptate cage. Replacement of the europium by other rare earth metals such as terbium is also conceivable. It is crucial that the fluorescence has a long duration to guarantee the time delay (Lopez E. et al., Clin Chem 39/2, 196-201, 1993; U.S. Pat. No. 5,534,622).

The detection methods described above are based on the principle that there is a correlation between the PARP activity and the amount of ADP-ribose polymers formed on the histones. The assay described herein makes it possible to quantify the ADP-ribose polymers using specific antibodies in the form of an ELISA and an HTRF (homogenous time-resolved fluorescence) assay. Specific embodiments of these two assays are described in detail in the following examples.

The developed HTRF (homogeneous time-resolved fluorescence) assay system measures the formation of poly(ADP-ribose) on histones using specific antibodies. In contrast to the ELISA, this assay is carried out in homogeneous phase without separation and washing steps. This makes a higher sample throughput and smaller susceptibility to errors possible. HTRF is based on the florescence resonance energy transfer (FRET) between two fluorophores. In a FRET assay, an excited donor fluorophore can transfer its energy to an acceptor fluorophore when the two are close to one another in space. In HTRF technology, the donor fluorophore is a europium cryptate [(Eu)K] and the acceptor is XL665, a stabilized allophycocyanin. The europium cryptate is based on studies by Jean Marie Lehn (Strasbourg). (Lopez E. et al., Clin Chem 39/2, 196-201, 1993; U.S. Pat. No. 5,534,622).

In a homogenous assay, all the components are also resent during the measurement. Whereas this has advantages for carrying out the assay (rapidity, complexity), it is necessary to preclude interference by assay components (inherent fluorescence, quenching by dyes etc.). HTRF precludes such interference by time-delayed measurement at two wavelengths (665 nm, 620 nm). The HTRF fluorescence has a very long decay time and time-delayed measurement is therefore possible. There is no longer any interference from short-lived background fluorescence (e.g. from assay components or inhibitors of the substance bank). In addition, measurement is always carried out, at two wavelengths in order to compensated for quench effects of colored substances. HTRF assays can be carried out, for example, in 96- or 384-well microtiter plate format and are evaluated using a Discovery HTRF Microplate Analyzer (Packard Instruments).

Also provided according to the invention are the following in vitro screening methods for binding partners for PARP.

A first variant is carried out by a1) immobilizing PARP on a support;
b1) contacting the immobilized PARP homolog with an analyze in which at least one binding partner is suspected; and
c1) determining, where appropriate after an incubation period, analyte constituents bound to the immobilized PARP.

A second variant entails a2) immobilizing on a support an analyte which comprises at least one possible binding partner for PARP;
b2) contacting the immobilized analyte with at least one PARP for which a binding partner is sought; and
c3) [sic] examining the immobilized analyte, where appropriate after an incubation period, for binding of PARP.

Assay systems for determining the activity of the enzyme and PARP-like enzymes and the inhibitory action of effectors on PARP and PARP-like enzymes.

a) Production of Antibodies Against Poly(ADP-Ribose)

It is possible to use poly(ADP-ribose) as antigen for generating anti-poly(ADP-ribose) antibodies. The production of anti-poly(ADP-ribose) antibodies is described in the literature (Kanai Y. et al. (1974) Biochem Biophys Res Comm 59:1, 300-306; Kawamaitsu H. et al. (1984) Biochemistry 23, 3771-3777; Kanai Y. et al. (1978) Immunology 34, 501-508).

The following were used, inter alia, anti-poly(ADF-ribose) antibodies (polyclonal antiserum, rabbits), BIOMOL; order No. SA-276. Anti-poly(ADP-ribose) antibodies (monoclonal, mouse; Clone 10H; hybrioma supernatant, affinity-purified).

The antisera or monoclonal antibodies obtained from hybridoma culture supernatant were purified by protein A affinity chromatography in the manner familiar to the skilled worker.

b) ELISA Assay

Materials:

ELISA color reagent: TMB mix, SIGMA T-8540

A 96-well microtiter plate (FALCON Micro-Test IIIä Flexible Assay Plate, #3912) was coated with histones (SIGMA, H-7755). Histones were for this purpose dissolved in carbonate buffer (0.05 M $Na_2HCO_3$; pH 9.4) in a concentration of 50 µg/ml. The individual wells of the microtiter plate were each incubated with 150 µl of this histone solution at room temperature for at least 2 hours or at 4° C. over night. The wells are then blocked by adding 150 µl of a 1% strength BSA solution (SIGMA, A-7888) in carbonate buffer at room temperature for 2 hours. This is followed by three washing steps with washing buffer (0.05% Tween10 in 1×PBS; PBS (phosphate buffered saline; Gibco, order No. 10010): 0.21 g/l $KH_2PO_4$, 9 g/l NaCl, 0.726 g/l $Na_2HPO_4.7H_2O$, pH 7.4). Washing steps were all carried out in a microtiter plate washer ("Columbus" microtiter plates washer, SLT-Labinstruments, Austria).

Required for the enzyme reaction were an enzyme reaction solution and a substrate solution, in each case as a premix. The absolute amount these solutions depended on the intended number of assay wells.

Composition of the enzyme reaction solution per well:
    4 µl of PARP reaction buffer (1 M Tris-HCl pH 8.0, 100 mM $MgCl_2$, 10 mM DTT)
    20 ng of PARP (human or bovine)
    4 µl of activated DNA (1 mg/ml; SIGMA, D-4522)
    $H_2O$ ad 40 µl Composition of the Substrate Solution Per Well:
    5 µl of PARP reaction buffer (10×)
    0.8 µl NAD solution (10 mM, SIGMA N-1511)
    44 µl of $H_2O$ Inhibitors were dissolved 1×PARP reaction buffer. DMSO, which was occasionally used to dissolve inhibitors in higher concentrations, was no problem up to a final concentration of 2%. For the enzyme reaction, 40 µl of the enzyme reaction solution were introduced into each well and incubated with 10 µl of inhibitor solution for 10 minutes. The enzyme reaction was then started by adding 50 µl of substrate solution per well. The reaction was carried out at room temperature for 30 minutes and then stopped by washing three times with washing buffer.

The primary antibodies employed were specific anti-poly (ADP-ribose) antibodies in a dilution of 1:5000. Dilution took place in antibody buffer (1% BSA in PBS; 0.05% Tween20). The incubation time for the primary antibody was one hour at room temperature. After subsequently washing three times with washing buffer, incubation was carried out with the secondary antibody (anti-mouse IgG, Fab fragments, peroxidase-coupled, Boehringer Mannheim, order No. 1500.686; anti-rabbit IgG, peroxidase-coupled, SIGMA, order No. A-6154) in a 1:10000 dilution in antibody buffer at room temperature for one hour. Washing three times with washing buffer was followed by the color reaction using 100 µl of color reagent (TMB mix, SIGMA) per well at room temperature for about 15 min. The color reaction was stopped by adding 100 µl of 2M $H_2SO_4$. This was followed by immediate measurement in an ELISA plate reader (EAR340AT "Easy Reader", SLT-Labinstruments, Austria) (450 nm versus 620 nm).

Various concentrations were used to construct a dose-effect blot to determine the $K_i$ of an inhibitor. Values are obtained in triplicate for a particular inhibitor concentration. Arithmetic means are determined using Microsoft© Excel. The $IC_{50}$ is determined using the Microcal© Origin Software (Vers. 5.0) ("Sigmoidal Fit"). Conversion of the $IC_{50}$ values calculated in this way into $K_i$ values took place by using "calibration inhibitors". The "calibration inhibitors" were also measured in each analysis. The $K_i$ values of the "calibration inhibitors" were determined in the same assay system by analysis of the Dixon diagram in the manner familiar to the skilled worker.

b) HTRF (Homogenous Time-Resolved Fluorescence) Assay

In the HTRF PARP assay according to the invention, histones, as target proteins for modification by PARP, are labeled indirectly with an XL665 fluorophore. The antibody is directly labeled with a europium cryptate. If the XL665-fluorophore is in the direct vicinity in space, which is ensured by binding to the poly(ADP-ribose) on the histone, then energy transfer is possible. The emission at 665 nm is thus directly proportional to the amount of bound antibody, which is in turn is equivalent to the amount of poly(ADP-ribose). The measured signal thus corresponds to the PARP activity. The materials use are identical to those used in the ELISA assay (see above) unless not expressly indicated.

Histones were dissolved in a concentration of 3 mg/ml in Hepes buffer (50 mM, pH=7.5). Biotinylation took place with sulfo-NHS-LC-biotin (Pierce, #21335T). A molar ratio of 4 biotin per histone was used. The incubation time was 90 minutes (RT). The biotinylated histones were then purified on a G25 SF HR10/10 column (Pharmacia, 17-0591-01) in Hepes buffer (50 mM, pH=7.0) in order to remove excess biotinylation reagent. The anti-poly(ADP-ribose) antibody was labeled with europium cryptate using bifunctional coupling reagents (Lopez E. et al. Clin. Chem. 39/2, 196-201, 1993 U.S. Pat. No. 5,534,662). Purification took place on a G25SF HR10/30 column. A molar ratio of 3.1 cryptates per antibody was achieved. The yield was 25%. The conjugates were stored at −80° C. in the presence of 0.1% BSA in phosphate buffer (0.1 M, pH=7).

For the enzyme reaction, the following were pipetted into each well:

10 μl of PARP solution in PARP HTRF reaction buffer (50 mM Tris-HCl pH 8.0, 10 mM MgCl12, 1 mM DTT) with 20 ng of PARP (human or bovine)

10 μl of activated DNA in PARP HTRF reaction buffer (50 μg/ml)

10 μl of biotinylated histones in PARP HTRF reaction buffer (1.25 μM)

10 μl of inhibitor in PARP HTRF reaction buffer

These reagents were preincubated for 2 minutes before starting the reaction by adding 10 μl of NAD solution in PARP HTRF reaction buffer (41 μM/ml). The reaction time was 30 minutes at room temperature.

The reaction was then stopped by adding

10 μl of PARP inhibitor (25 μM, $K_i$=10 nM) in "Revelation" buffer (100 mM Tris-HCl pH 7.2, 0.2 M KF, 0.05% BSA).

The following were then added:

10 μl EDTA-solution (SIGMA, E-7889, 0.5 M in $H_2O$)

100 μl Sa-XL665 (Packard Instruments) in "Revelation" buffer (15-31.25 nM)

50 μl of anti-PARP cryptate in "Revelation" buffer (1.6-3.3 nM).

Measurement was then possible after 30 minutes (up to 4 hours). The measurement took place in a "Discovery HTRF Microplate Analyzer" (Packard Instruments). The $K_i$ values were calculated as described fro the ELISA assay.

Determination of the Solubility in Water

A compound to be measured is dissolved directly in a fixed volume of water, and the resulting solution is adjusted to pH 5 to 6 with a sodium acetate solution so that the active ingredient concentration to be tested is reached. If the measured substance is not in the form of a water-soluble salt, it was dissolved in the minimum amount of dimethyl sulfoxide and then diluted with water (final dimethyl sulfoxide concentration$\leq$1%), after which the pH was again adjusted. The potent PARP inhibitor NU 1076 (WO 97/04771) showed a solubility<0.01%, whereas Example 2 according to the invention has a solubility>0.5%.

The substituted 2-phenylbenzimidazoles of the general formula I are inhibitors of poly(ADP-ribose) polymerase (PARP) or, as it is also called, poly(ADP-ribose) synthase (PARS), and can thus be used for the treatment and prophylaxis of diseases associated with an increased activity of these enzymes.

The compounds of the formula I can be employed to produce drugs for treating damage following ischemias and for the prophylaxis of expected ischemias in various organs.

The present 2-phenylbenzimidazoles of the general formula I can accordingly be used for the treatment and prophylaxis of neurodegenerative diseases occurring after ischemia, trauma (craniocerebral trauma), massive bleeding, subarachnoid hemorrhages and stroke, and of neurodegenerative diseases such as multi-infarct dementia, Alzheimer's disease, Huntington's disease and of epilepsies, in particular of generalized epileptic seizures, such as, for example, petit mal and tonoclonic seizures and partial epileptic seizures such as temporal lope, and complex partial seizures, and further for the treatment and prophylaxis of damage to the heart after cardiac ischemia and damage to the kidneys after renal ischemia, for example of acute renal insufficiency, of acute kidney failure or of damage occurring during and after a kidney transplant. The compounds of the general formula I can further be used treat acute myocardial infarct and damage occurring during and after medical lysis thereof (for example with TPA, Reteplase, streptokinase or mechanically with a laser or Rotablator) and of microinfarcts during and after heart valve replacement, aneurysm resections and heart transplants. It is likewise possible to use the present 2-phenylbenzimidazoles I for treatment in cases of revascularitzation of critically narrowed coronary arteries, for example in PCTA and bypass operations, and critically narrowed peripheral arteries, for example leg arteries. In addition, the 2-phenylbenzimidazoles I can be beneficial in the chemotherapy of tumors and metastasis thereof and can be used to treat inflammations and rheumatic disorders such as, for example, rheumatoid arthritis.

Novel PARP inhibitors can have therapeutic efficacy checked in relevant pharmacological models. Examples of some suitable models are listed in Table 1.

TABLE I

| Disorder | Model | Literature |
| --- | --- | --- |
| Neurodegenerative disorders (stroke, Parkinson's etc.) | NMDA excitotoxicity in mice or rats | |
| Stroke | Permanent MCAO ("middle cerebral artherial occlusion") | Tokime T. et al., J. Cereb Blood Flow Ketab, 18(9):991-7, 1998, Guegan C. Brain Research. Molecular Brain Research 55(1) 133-40, 1998 |
| | Transient, focal MCAO in rats or mice | Eliasson MJL et al., Nat Med 1997, 3:1089-1095. Endres M. et al., J. Cereb Blood Flow Metab 1997, 17:1143-1151. Takahasbi K. et al., J. Cereb Blood Flow Metab 1997, 17:1137-1142. |
| Parkinson's disease | MPTP (1-methyl-4-phenyl-1,2,3,6-tetrahydro-pyridine) toxicity in mice/rats | Cosi C. et al., Brain Res., 1998 809(1):58-67. Cosi C. et al., Brain Res., 1996 729(2):264-9. |
| Myocardial infarct | Coronary vessel occlusion in rats, pigs or rabbits | Richard V. et al., Br. J. Pharmacol 1994, 113, 869-876. Thiemermann C. et al., Proc Natl Acad Sci USA. 1997, 94(2):679-83. Zingarelli B. et al., Cardiovasc Res. 1997, 36(2):205-15. |
| | Langendorf heart model in rats or rabbits | See below for description |

TABLE I-continued

| Disorder | Model | Literature |
|---|---|---|
| Septic shock | Endotoxin shock in rats | Szabo C. et al., J. Clin Invest, 1997, 100(3):723-35. |
| | Zymosan- or carrageenan-induced multiple organ failure in rats or mice | Szabo C. et al., J. Exp Med. 1997, 186(7):1041-9. Cuzzocrea S. et al., Eur J. Pharmacol. 1998, 342(1):67-76. |
| Rheumatoid arthritis | Adjuvant- or collagen-induced arthritis in rats or mice | Szabo C. et al., Proc Natl Acad Sci USA. 1998, 95(7):3867-72. |
| Diabetes | Streptozotocin- and alloxan-induced or obesity-associated | Uchigata Y. et al., Diabetes 1983, 32: 316-318. Masiello P. et al., Diabetologia 1985, 28: 683-686. Shimabukuro M. et al., J. Clin Invest 1997, 100: 290-295. |
| Cancer | | Schlicker et al. Int J Radiat Biol. 1999 Jan:75(1):91-100. |

The pharmaceutical preparations according to the invention comprise a therapeutically effective amount of the compounds I in addition to the conventional pharmaceutical ancillary substances.

For local external use, for example in dusting powders, ointments or sprays, the active substances can be present in the usual concentrations. The active substances are ordinarily present in an amount of from 0.001 to 1% by weight, preferably 0.001 to 0.1% by weight.

On internal use, the preparations are administered in single doses. From 0.1 to 100 mg are given per kg of body weight in a single dose. The preparation may be administered in one or more doses each day, depending on the nature and severity of the disorders.

Appropriate for the required mode of administration, the pharmaceutical preparations according to the invention comprise conventional excipients and diluents in addition to the active substance. For local external use it is possible to use pharmaceutical ancillary substances such as ethanol, isopropanol, ethoxylated castor oil, ethoxylated hydrogenated castor oil, polyacrylic acid, polyethylene glycol, polyethylene glycol stearate, ethoxylated fatty alcohols, liquid paraffin, petrolatum and wool fat. Examples suitable for internal use are lactose, propylene glycol, ethanol, starch, talc and polyvinylpyrrolidone.

It is also possible for antioxidants such as tocopherol and butylated hydroxyanisole, and butylated hydroxytoluene, flavor-improving additives, stabilizers, emulsifiers and lubricants to be present.

The substances present in the preparation in addition to the active substance, and the substances used in the production of the pharmaceutical preparations, are toxicologically acceptable and compatible with the particular active substance. The pharmaceutical preparations are produced in a conventional way, for example by mixing the active substance with conventional excipients and diluents.

The pharmaceutical preparations can be administered in various ways, for example orally, parenterally such as intravenously by infusion, subcutaneously, intraperitoneally and topically. Thus, possible presentations are tablets, emulsions, infusion and injection solutions, pastes, ointments, gels, creams, lotions, dusting powders and sprays.

EXAMPLE 1

2-(4-(2-(N,N-Diethylamino)eth-1-yloxy)phenyl)benzimidazole-4-carboxamide

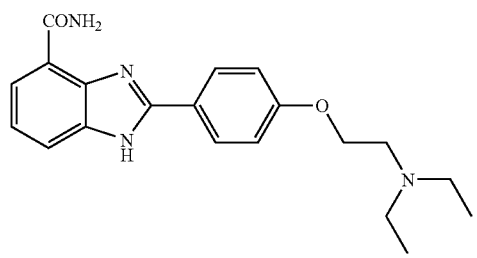

a) 4-(2-(N,N-diethylaminoeth-1-yloxy)benzaldehyde 15 g (122 mmol) of 4-hydroxybenzaldehyde, 16.7 g (122 mmol) of N-(2-chloroethyl)-N,N-diethylamine and 33.9 g (246 mmol) of potassium carbonate were refluxed together with a spatula tip of 18-crown-6 in 300 ml of ethyl methyl ketone for 6 hours. After filtration, the filtrate was concentrated in vacuo. The residue was partitioned between ether and 2M sodium hydroxide solution, and the ether phase was separated off, dried and concentrated in vacuo. 24.8 g of the intermediate were obtained.

b) Ethyl 2-(4-(2-(N,N-diethylamino)eth-1-yloxy)phenyl)benzimidazole-4-carboxylate 2 g (11 mmol) of ethyl 2,3-diaminobenzoate and 1.4 ml of concentrated acetic acid were diissolved in 25 ml of methanol. Then 3.2 g (14.4 mmol) of intermediate 1a, dissolved in 50 ml of methanol, were added dropwise over the course of 30 minutes. Subsequently 2.9 g (14.4 mmol) of copper II acetate, dissolved in 37.5 ml of warm water, were rapidly added dropwise, and then the mixture was refluxed for 20 minutes. The reaction solution was cooled to 50° C., and 4.5 ml of 32% strength hydrochloric acid were added. Then a solution of 4.3 g of sodium sulfide hydrate in 25 ml of water was cautiously added dropwise, and the mixture was stirred for 15 minutes. The reaction solution was poured into ice-water, and the resulting precipitate was filtered off with suction. The filtrate was made alkaline with aqueous sodium bicarbonate solution and extracted several times with ethyl acetate. The ethyl acetate phase was separated, dried and concentrated in vacuo. 4.4 g of the intermediate were obtained.

c) 2-(4-(2-(N,N-Diethylamino)eth-1-yloxy)phenyl) benzimidazole-4-carbohydrazide 2.7 g (54 mmol) of hydrazine hydrate were added to 4.1 g (10.7 mmol) of intermediate 1b in 30 ml of ethanol, and the mixture was refluxed for 10 hours. The organic solvent was then removed in vacuo, and the residue was partitioned between water and ethyl acetate. The ethyl acetate phase was separated off, dried and concentrated in vacuo. The residue obtained in this way was then treated with ether and again filtered off with suction, whereby 1.7 g of the intermediate [sic].

d) 2-(4-(2-(N,N-Diethylamino)eth-1-yloxy)phenyl) benzimidazole-4-carboxamide About 1.6 g of Raney nickel were added to 1.6 g (4.5 mmol) of intermediate 1c in 45 ml of dimethylformamide/water (2/1), and the mixture was heated at 100° C. for 6 hours. The reaction mixture was then filtered, and the filtrate was diluted with a large amount of water, whereupon the product precipitated. 1.2 g of the product were obtained.

$^1$H-NMR ($D_6$-DMSO). δ=0.95 (6H), 2.6 (4H), 2.8 (2H), 4.1 (2H), 7.1 (2H), 7.3 (1H), 7.7 (1H+NH), 7.85 (1H), 8.2 (2H) and 9.4 (NH) ppm.

EXAMPLE 2

2-(4-(2-(N,N-Diethylamino)eth-1-yloxy)phenyl) benzimidazole-4-carboxamide×2 hydrochloride

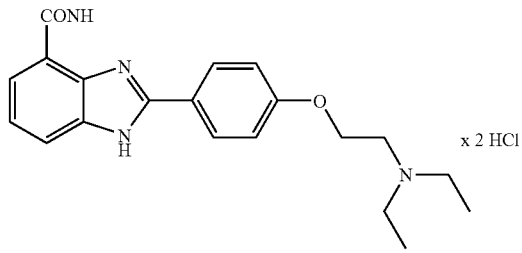

0.2 g of the product of Example 1 were dissolved in a mixture of ethyl acetate and a little tetrahydrofuran, and ethereal hydrogen chloride solution was added to form a precipitate. This precipitate was filtered off with suction, suspended in acetone and again filtered off with suction, resulting in about 200 mg of the product.

$^1$H-NMR ($D_6$-DMSO): δ=1.2 (6H), 3.2 (4H), 3.3 (2H), 4.5 (2H), 7.25 (1H), 7.4 (1H), 7.8-7.9 (2H), 8.3 (2H), 9.0 (NH) and 10.5 (NH) ppm.

EXAMPLE 3

2-(3-(2-(N,N-Diethylamino)eth-1-yloxy)phenyl) benzimidazole-4-carboxamide

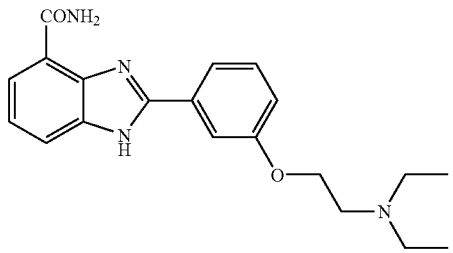

a) 3-(2-(N,N-Diethylaminoeth-1-yloxy)benzaldehyde [sic]

6.1 g (50 mmol) of 3-hydroxybenzaldehyde were dissolved in 100 ml of ethanol and 3.5 g (50 mmol) of sodium ethanolate were added. The mixture was stirred for 15 minutes. Then 7.5 g (55 mmol) of N-(2-chloroethyl)-N,N-diethylamine were added, and the mixture was refluxed for 12 hours. The reaction mixture was then concentrated in vacuo. The residue was then partitioned between ether and 1M sodium hydroxide solution, and the ether phase was separated off, dried and concentrated in vacuo. 7.6 g of the intermediate were obtained.

b) Ethyl 2-(3-(2-(N,N-diethylamino)eth-1-yloxy) phenyl)benzimidazole-4-carboxylate 1 g (5.5 mmol) of ethyl 2,3-diaminobenzoate and 0.68 ml of concentrated acetic acid were dissolved in 20 ml of methanol. Then 1.6 g (7.2 mmol) of intermediate 3a, dissolved in 30 ml of methanol, were added dropwise over the course of 30 minutes. Subsequently, 1.1 g (5.5 mmol) of copper(II) acetate, dissolved in 19 ml of warm water, were rapidly added dropwise, and the mixture was then refluxed for 20 minutes. The reaction solution was cooled to 50° C. and 2.25 ml of 32% strength hydrochloric acid were added. Then a solution of 2.13 g of sodium sulfide hydrate in 15 ml of water was cautiously added dropwise, and the mixture was stirred for 15 minutes. The reaction solution was poured into ice-water, and the resulting precipitate was filtered off with suction. The filtrate was made alkaline with aqueous sodium bicarbonate solution and extracted several times with ethyl acetate. The ethyl acetate phase was separated off, dried and concentrated in vacuo. 2.4 g of the intermediate were obtained.

c) 2-(3-(2-(N,N-Diethylamino)eth-1-yloxy)phenyl) benzimidazole-4-carbohydrazide 1.5 g (30 mmol) of hydrazine hydrate were added to 2.3 g (6.0 mmol) of intermediate 3b in 30 ml of butanol, and the mixture was heated at 120° C. for 10 hours. The reaction mixture was then diluted with a large amount of water and extracted with ethyl acetate. The ethyl acetate phase was separated off, dried and concentrated in vacuo. 1.7 g of the intermediate were obtained.

d) 2-(3-(2-(N,N-Diethylamino)eth-1-yloxy)phenyl) benzimidazole-4-carboxamide About 1.5 g of Raney nickel were added to 1 g (2.7 mmol) of intermediate 3c in 30 ml dimethylformamide/water (2/1), and the mixture was heated at 100° C. for 6 hours. The reaction mixture was then filtered and the filtrate was diluted with a large amount of water to precipitate the product. 0.74 g of the product was obtained.

$^1$H-NMR ($D_6$-DMSO): δ=1.0 (6H), 2.6 (4H), 2.9 (2H), 4.15 (2H), 7.1 (1H), 7.4 (1H), 7.5 (1H), 7.7-7.9 (5H) and 9.3 (NH) ppm.

EXAMPLE 4

2-(3-(2-(N,N-Diethylamino)eth-1-yloxy)phenyl)benzimidazole-4-carboxamide×2 hydrochloride

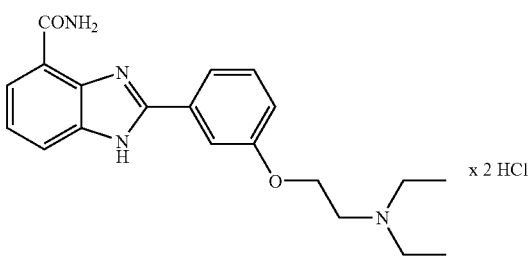

0.2 g of the product from Example 3 was dissolved in a mixture of ethyl acetate and tetrahydrofuran, and ethereal hydrogen chloride solution was added to form a precipitate. This precipitate was filtered off with suction, suspended in acetone and again filtered off with suction, to result in about 200 mg of the product.

$^1$H-NMR (D$_6$-DMSO): δ=1.3 (6H), 3.2 (4H), 3.6 (2H), 4.6 (2H), 7.2-8.1 (8H), 9.0 (1H) and 10.8 (NH) ppm.

The following were prepared in analogy to Example 1:

EXAMPLE 5

2-(3-(2-(N,N-Dimethylamino)eth-1-yloxy)phenyl)benzimidazole-4-carboxamide

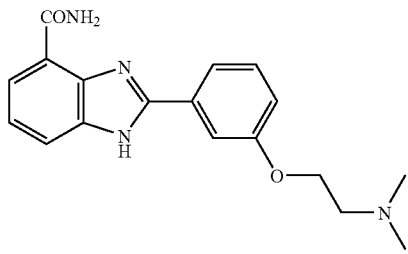

$^1$H-NMR (D$_6$-DMSO). δ=2.2 (6H), 2.7 (2H), 4.2 (2H), 7.0-8.0 (9H) and 9.3 (1H) ppm.

EXAMPLE 6

2-(3-(2-(N,N-Dimethylamino)eth-1-yloxy)-4-methoxy-phenyl)-benzimidazole-4-carboxamide

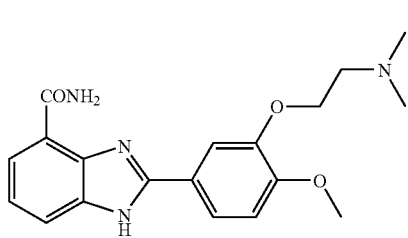

$^1$H-NMR (D$_6$-DMSO): δ=2.25 (6H), 2.75 (2H), 3.8 (3H), 4.1 (2H), 7.0-8.1 (8H) and 9.4 (1H) ppm.

EXAMPLE 7

2-(3-(2-(N,N-Dimethylamino)eth-1-yloxy)-4-methoxy-phenyl)-benzimidazole-4-carboxamide×2 HCl

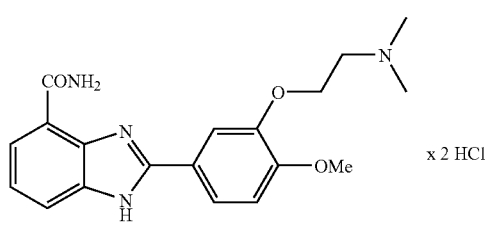

$^1$H-NMR (D$_2$O): δ=3.0 (6H), 3.7 (2H), 3.8 (3H), 4.3 (2H), 6.9 (1H), 7.3 (1H), 7.3-7.5 (3H) and 7.7 (3H) ppm.

EXAMPLE 8

2-(2-(2-(N,N-Dimethylamino)eth-1-yloxy)phenyl)benzimidazole-4-carboxamide×2 HCl

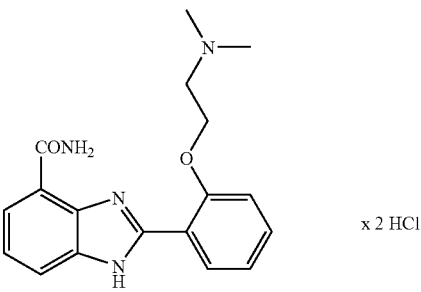

$^1$H-NMR (D$_6$-DMSO): δ=2.9 (6H), 3.7 (2H), 4.7 (2H), 7.2-8.3 (8H), 8.9 (broad) and ca 11 (broad) ppm.

EXAMPLE 9

2-(3-(2-(N,N-Dimethylamino)eth-1-yloxy)phenyl)benzimidazole-4-carboxamide×2 hydrochloride

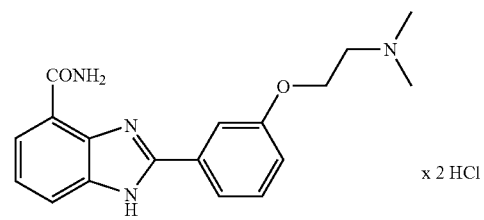

$^1$H-NMR (D$_6$-DMSO): δ=2.9 (6H), 3.5 (2H), 4.5 (2H), 7.2-8.1 (8H), 9.0 (broad) and ca 10.8 (broad) ppm.

EXAMPLE 10

2-(3-(3-(tert-Butoxycarbonylamino)prop-1-yloxy)phenyl)-benzimidazole-4-carboxamide

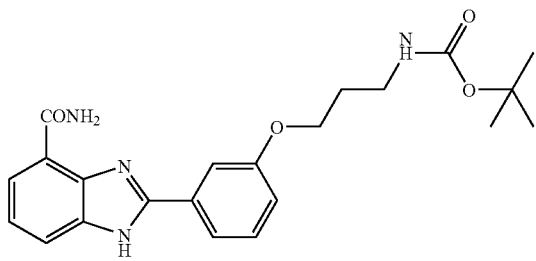

$^1$H-NMR (D$_6$-DMSO): δ=1.3 (9H), 1.9 (2H), 3.1 (2H), 4.1 (2H), 6.9-8.0 (9H) and ca 9.3 (broad) ppm.

EXAMPLE 11

2-(3-(3-(tert-Butoxycarbonylamino)eth-1-yloxy)phenyl)-benzimidazole-4-carboxamide

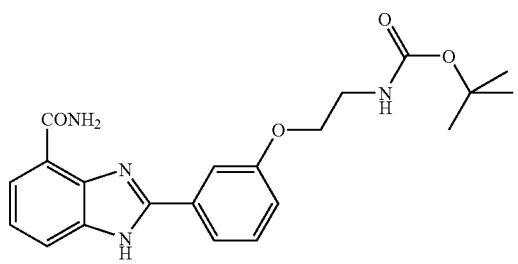

$^1$H-NMR (D$_6$-DMSO): δ=1.3 (9H), 3.3 (2H), 4.1 (2H), 7.0-8.0 (9H) and ca 9.3 (broad) ppm.

EXAMPLE 12

2-(3-(3-(4-(3-Chlorophenyl)-1-piperazinyl)prop-1-yloxy)phenyl)-benzimidazole-4-carboxamide

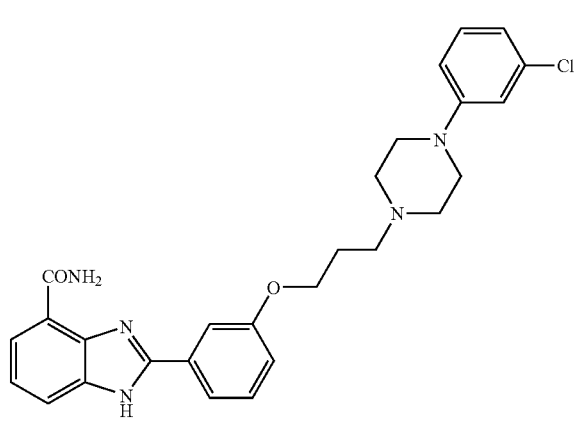

$^1$H-NMR (D$_6$-DMSO): δ=2.3 (2H), 3.3-3.5 (6H), 3.7 (2H), 3.7-4.3 (6H), 6.9-8.0 (11H), 9.1 (broad) and ca 10.9 (broad) ppm.

EXAMPLE 13

2-(3-(3-(N,N-Diethylamino)prop-1-yloxy)phenyl)benzimidazole-4-carboxamide×2 HCl

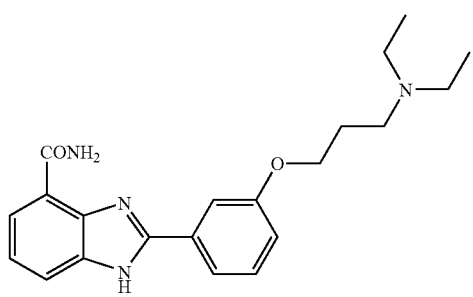

$^1$H-NMR (D$_6$-DMSO): δ=1.2 (6H), 2.2 (2H), 3.2 (4H), 3.8 (2H), 4.3 (2H), 7.1-8.0 (7H), 9.1 (broad) and ca 10.5 (broad) ppm.

EXAMPLE 14

2-(3-(3-Aminoprop-1-yloxy)phenyl)benzimidazole-4-carboxamide×2 HCl

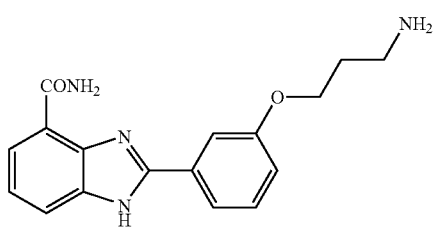

$^1$H-NMR (D$_6$-DMSO): δ=2.1 (2H), 3.0 (2H), 4.2 (2H), 7.2 (1H), 7.5 (2H), 7.8-8.1 (6H), 8.2 (broad) and ca 8.9 (broad) ppm.

EXAMPLE 15

2-(3-(2-Aminoeth-1-yloxy)phenyl)benzimidazole-4-carboxamide×2 HCl

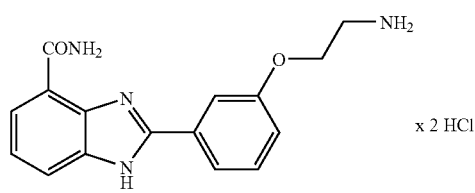

$^1$H-NMR (D$_6$-DMSO): δ=3.2 (2H), 4.2 (2H), 7.1-8.0 (9H), 8.2 (broad) and 9.0 (broad) ppm.

The following examples can be prepared in analogy to the above methods:

EXAMPLE 16

2-(4-(3-(N,N-Diethylamino)prop-1-yloxy)phenyl)benzimidazole-4-carboxamide×2 HCl $^1$H-NMR (D$_6$-DMSO): δ=1.3 (6H), 2.2 (2H), 3.2 (6H), 4.2 (2H), 7.2 (2H), 7.5 (1H), 7.8-8.0 (3H), 8.35 (2H), 8.9 (1H) and 10.7 (broad) ppm.

EXAMPLE 17

1-(3-(N,N-Diethylamino)prop-1-yl)-2-(4-(3-(N,N-diethylamino)prop-1-yloxy)phenyl)benzimidazole-4-carboxamide×2 HCl $^1$H-NMR (D$_6$-DMSO): δ=1.1-1.3 (12H), 2.2 (4H), 2.9-3.3 (12H), 4.2 (2H), 4.5 (2H), 7.2 (2H), 7.6 (1H), 7.8-8.1 (3H), 8.3 (1H), 8.4 (1 h), 8.9 (1H) and 11.0 (broad) ppm.

EXAMPLE 18

2-(4-(2-(Pyrrolidin-1yl)eth-1-yloxy)phenyl)benzimidazole-4-carboxamide×2 HCl $^1$H-NMR (D$_6$-DMSO): δ=1.3 (1H), 1.7-2.0 (5H), 3.0 (2H), 3.5 (4H), 4.5 (2H), 7.2 (2H), 7.3 (1H), 7.7-8.0 (3H), 8.2 (2H), 8.9 (broad) and 10.7 (broad) ppm.

EXAMPLE 19

1-(3-(Pyrrolidin-1-yl)prop-1-yl)-2-(4-(2-(pyrrolidin-1-yl)eth-1-yloxy)phenyl)benzimidazole-4-carboxamide×2 HCl $^1$H-NMR (D$_6$-DMSO): δ=1.3 (2H), 1.7-1.9 (10H), 3.0 (4H), 3.3-3.6 (8H), 4.5 (2H), 4.9 (2H), 7.1 (2H), 7.5 (1H), 7.7-8.0 (3H), 8.1 (2H), 9.0 (broad), 10.8 (broad) and 11.2 (broad) ppm.

EXAMPLE 20

2-(4-(3-(N,N-Benzylmethylamino)prop-1-yloxy)phenyl)benzimidazole-4-carboxamide×2 HCl

EXAMPLE 21

1-(3-(N,N-Benzylmethylamino)prop-1-yl)-2-(4-(3-(N,N-benzylmethyl-amino)prop-1-yloxy)phenyl)benzimidazole-4-carboxamide×2 HCl MS: m/e=575 (M$^+$).

EXAMPLE 22

2-(4-(3-(4-Methylpiperazin-1-yl)prop-1-yloxy)phenyl)benzimidazole-4-carboxamide×3HCl MS: m/e=393 (M$^+$).

EXAMPLE 23

2-(3-(2-(N,N-Benzylmethylamino)eth-1-yloxy)-4-nitrophenyl)-benzimidazole-4-carboxamide $^1$H-NMR (D$_6$-DMSO): δ=1.0 (6H), 2.5-2.8 (4H), 2.9 (2H), 4.3 (2H), 7.3 (1H), 7.8-8.2 (6H) and 9.1 (1H) ppm.

EXAMPLE 24

2-(4-(3-Trifluoracetamidomethylpyrrol-1-yl)phenyl)benzimidazole-4-carboxamide a) Ethyl 2-(4-nitrophenyl)benzimidazole-4-carboxylate 1.5 g (8.3 mmol) of ethyl 2,3-diaminobenzoate and 1.1 ml of concentrated acetic acid were dissolved in 50 ml of methanol. 1.6 g (10.8 mmol) of 4-nitrobenzaldehyde, dissolved in 150 ml of methanol, were then added dropwise over a period of 30 minutes. 2.2 g (10.8 mmol) of copper(II) acetate, dissolved in 100 ml of warm water, were then rapidly added dropwise, and the entire mixture was subsequently refluxed for 20 minutes. The reaction solution was cooled to 50° C. and 3 ml of 32% strength hydrochloric acid were added. This was followed by careful dropwise addition of a solution of 3.1 g of sodium sulfide hydrate in 50 ml of water, and the entire mixture was stirred for another 15 minutes. The reaction solution was poured into ice-water and the resulting precipitate was filtered off with suction. The filtrate was made alkaline using aqueous sodium bicarbonate solution and extracted repeatedly with ethyl acetate. The ethyl acetate phase was separated off, dried and concentrated under reduced pressure. This gave 2.2 g of the intermediate.

b) 2-(4-(4-Nitrophenyl)benzimidazole-4-carbohydrazide 1.7 ml (34 mmol) of hydrazine hydrate were added to 2.1 g (6.7 mmol) of the intermediate 24a in 25 ml of ethanol, and the entire mixture was refluxed for 4 hours. The organic solvent was subsequently removed under reduced pressure and the residue was partitioned between water and ethyl acetate. The ethyl acetate phase was separated off, dried and concentrated under reduced pressure. The resulting residue was then treated with ether and again filtered off with suction, giving 1.7 g of the intermediate.

c) 2-(4-(4-Aminophenyl)benzimidazole-4-carboxamide

Approximately 1 g of palladium on carbon (10%) were added to 1.7 g (5.7 mmol) of the intermediate 24b in 120 ml of ethanol/acetic acid (5/1), and the entire mixture was hydrogenated using hydrogen. The reaction mixture was then filtered and the filtrate was concentrated under reduced pressure. The residue was taken up in 70 ml of a mixture of dimethylformamide and water (7/3). 2 g of Raney nickel were then added and the entire mixture was heated at 100° C. for 4 h. The reaction mixture was then filtered and the filtrate was concentrated under reduced pressure. The resulting residue was suspended in ether and filtered off with suction, giving 1.5 g of the product.

d) 2-(4-(3-Trifluoroacetamidomethylpyrrol-1-yl)phenyl)benzimidazole-4-carboxamide 1.4 g (5.6 mmol) of the intermediate 24c and 1.8 g (6.9 mmol) of 2,5-dimethoxy-3-(trifluoroacetamidomethyl)tetrahydrofuran were added to 50 ml of concentrated acetic acid, and the mixture was subsequently refluxed for 10 minutes. The entire mixture was subsequently concentrated under reduced pressure and the resulting residue was purified by silica gel chromatography using ethyl acetate as mobile phase. This gave 1.9 g of the product.

$^1$H-NMR (D$_6$-DMSO). δ=4.3 (2H), 6.3 (1H), 7.35 (1H), 7.5 (1H), 7.7-7.9 (5H), 8.3 (2H), 9.4 (1H) and 9.9 (1H) ppm.

EXAMPLE 25

2-(-4(3-Aminomethylpyrrol-1-yl)phenyl)benzimidazole-4-carboxamide

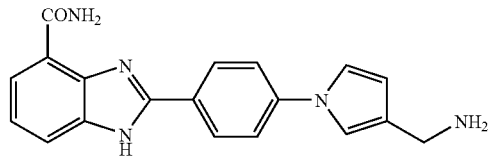

1.7 g (4 mmol) of the compound from Example 24 were dissolved in 70 ml of tetrahydrofuran and admixed with a solution of 0.38 g (15.9 mmol) of lithium hydroxide in 25 ml of water. The entire mixture was stirred at room temperature for 2 hours. The reaction mixture was then neutralized using dilute hydrochloric acid and the organic solvent was removed under reduced pressure. The resulting precipitate was filtered off with suction and dried. This gives 0.87 g of the product.

$^1$H-NMR (D$_6$-DMSO). δ=4.4 (2H), 7.0 (NH) and 7.8-8.4 (11H) ppm.

EXAMPLE 26

2-(4-(3-Aminomethylpyrrol-1-yl)phenyl)benzimidazole-4-carboxamide×2 methanesulfonic acid

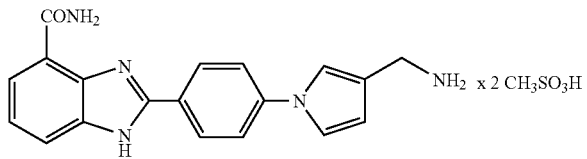

0.1 g of the product from Example 25 was dissolved in 2 ml of tetrahydrofuran and admixed with 20.5 μl of methanesulfonic acid, diluted with 5 ml of water. The mixture was subsequently diluted with water and the resulting solution was lyophilized, giving 117 mg of the product.

$^1$H-NMR (D$_6$-DMSO). δ=2.45 (6H), 4.0 (2H), 6.4 (1H), 7.2-8.4 (11H) and 9.1 (NH) ppm.

EXAMPLE 27

2-(4-(1-Imidazolyl)phenyl)benzimidazole-4-carboxamide

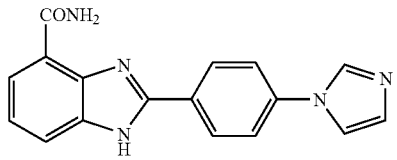

a) Ethyl 2-(4-(1-imidazolyl)phenyl)benzimidazole-4-carboxylate 1 g (5.5 mmol) of ethyl 2,3-diaminobenzoate and 0.7 ml of concentrated acetic acid were dissolved in 13 ml of methanol. 1.24 g (7.2 mmol) of 4-imidazol-1-ylbenzaldehyde, dissolved in 25 ml of methanol, were then added dropwise over a period of 30 minutes. 1.4 g (7.2 mmol) of copper(II) acetate, dissolved in 19 ml of warm water, were then rapidly added dropwise, and the entire mixture was subsequently refluxed for 20 minutes. The reaction solution was cooled to 50° C. and 2.25 ml of 32% strength hydrochloric acid were added. This was followed by careful dropwise addition of a solution of 2.13 g of sodium sulfide hydrate in 15 ml of water, and the entire mixture was stirred for another 15 minutes. The reaction solution was poured into ice-water and the resulting precipitate was filtered off with suction. The filtrate was made alkaline using aqueous sodium bicarbonate solution and extracted repeatedly with ethyl acetate. The ethyl acetate phase was separated off, dried and concentrated under reduced pressure. This gave 1.7 g of the intermediate.

b) 2-(4-(1-Imidazolyl)phenyl)benzimidazole-4-carbohydrazide 5 ml of hydrazine hydrate were added to 1.6 g (5.0 mmol) of the intermediate 27a in 30 ml of butanol, and the entire mixture was refluxed for 8 hours. The reaction mixture was then concentrated under reduced pressure and the residue was partitioned between water and ethyl acetate. The ethyl acetate was separated off, dried and concentrated under reduced pressure. This gave 0.55 g of the intermediate.

c) 2-(4-(1-Imidazolyl)phenyl)benzimidazole-4-carboxamide

Approximately 1.5 g of Raney nickel were added to 0.53 g (1.7 mmol) of the intermediate 27b in 35 ml of dimethylformamide/water (2/1), and the entire reaction mixture was heated at 100° C. for 8 hours. The reaction mixture was then filtered and the filtrate was diluted with a lot of water, causing the product to precipitate out. This gave 0.19 g of the product.

$^1$H-NMR (D$_6$-DMSO). δ=7.2 (1H), 7.4 (1H), 7.7-8.0 (6H) 8.4 (3H) and 9.4 (1H) ppm.

EXAMPLE 28

2-(4-(1-Imidazolyl)phenyl)benzimidazole-4-carboxamide×2 methanesulfonic acid

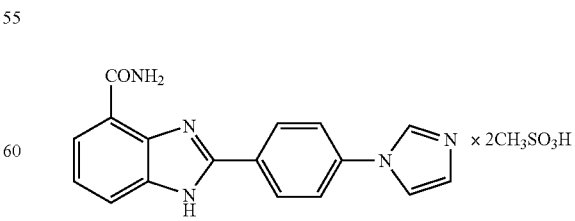

Analogously to the procedure 26a, 50 mg of the compound from Example 4 were converted into the bismethanesulfonate and lyophilized. This gave 60 mg of the product.

$^1$H-NMR (D$_6$-DMSO). δ=2.3 (6H), 7.4 (2H), 7.8-8.2 (7H), 8.4 (1H), 8.5 (2H), 9.1 (1H) and 9.8 (2H) ppm.

EXAMPLE 29

2-(3-(3-Trifluoroacetamidomethylpyrrol-1-yl)phenyl)benzimidazole-4-carboxamide

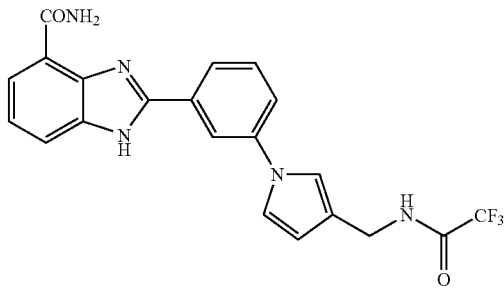

a) Ethyl 2-(3-nitrophenyl)benzimidazole-4-carboxylate 4.2 g (23 mmol) of ethyl 2,3-diaminobenzoate and 3.1 ml of concentrated acetic acid were dissolved in 100 ml of methanol. 4.5 g (30 mmol) of 4-nitrobenzaldehyde, dissolved in 150 ml of methanol, were then added dropwise over a period of 30 minutes. 6 g (30 mmol) of copper(II) acetate, dissolved in 150 ml of warm water, were then rapidly added dropwise, and the entire mixture was subsequently refluxed for 20 minutes. The reaction solution was cooled to 50° C. and 8.3 ml of concentrated hydrochloric acid were added. This was followed by careful dropwise addition of a solution of 8.6 g of sodium sulfide hydrate in 100 ml of water, and the entire mixture was stirred for another 15 minutes. The reaction solution was poured into ice-water and the resulting precipitate was filtered off with suction. The filtrate was made alkaline using aqueous sodium bicarbonate solution and extracted repeatedly with ethyl acetate. The ethyl acetate phase was separated off, dried and concentrated under reduced pressure. This gave 6.1 g of the intermediate.

b) 2-(3-Nitrophenyl)benzimidazole-4-carbohydrazide 4.8 g (96 mmol) of hydrazine hydrate were added to 6 g (19.3 mmol) of the intermediate 29a in 70 ml of ethanol, and the entire mixture was refluxed for 3 hours. The reaction mixture was subsequently poured into water and the resulting precipitate was filtered off with suction. This gave 4.8 g of the intermediate.

c) 2-(3-Aminophenyl)benzimidazole-4-carboxamide 0.5 g of palladium on carbon (10%) was added to 4.7 g (15.8 mmol) of the intermediate 29b in 400 ml of ethanol, and the entire reaction mixture was hydrogenated using hydrogen. The reaction mixture was then filtered and concentrated under reduced pressure. The residue was taken up in 100 ml of dimethylformamide and then diluted with 70 ml of water. 10 g of Raney nickel were then added, and the entire mixture was heated at 90° C. for 2 h. The mixture was subsequently filtered and the filtrate was concentrated under reduced pressure. The resulting residue was crystallized from ethyl acetate/ether, giving 3.1 g of the product.

d) 2-(3-(3-Trifluoroacetamidomethylpyrrol-1-yl)phenyl)benzimidazole-4-carboxamide 2.2 g (8.7 mmol) of the intermediate 29c and 2.8 g (10.9 mmol) of 2,5-dimethoxy-3-(trifluoroacetamidomethyl)-tetrahydrofuran were added to 75 ml of concentrated acetic acid, and the mixture was refluxed for 15 minutes. The entire mixture was subsequently concentrated under reduced pressure and the resulting residue was purified by silica gel chromatography using the mobile phase ethyl acetate/methanol (10/1). This gave 2.5 g of the product.
MS: m/e=427 (M$^+$).

EXAMPLE 30

2-(3-(3-Aminomethylpyrrol-1-yl)phenyl)benzimidazole-4-carboxamide

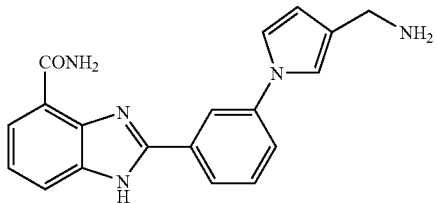

2.3 g (5.4 mmol) of the compound from Example 29 were dissolved in 100 ml of tetrahydrofuran and mixed with 0.26 g (10.8 mmol) of lithium hydroxide, dissolved in 50 ml of water. The entire mixture was stirred at room temperature for 2 hours. The mixture was subsequently neutralized by addition of dilute hydrochloric acid and the organic solvent was removed under reduced pressure. The precipitate, which slowly crystallized out, was filtered off with suction. This gave 0.61 g of the product.
$^1$H-NMR (CF$_3$COOD). δ=4.4 (2H), 7.0 (NH) and 7.8-8.4 (11H) ppm.

EXAMPLE 31

2-(4-(4-Methylpiperazin-1-yl)phenyl)benzimidazole-4-carboxamide

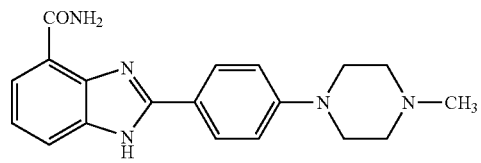

a) 4-(4-Methylpiperazin-1-yl)benzaldehyde 20 g (161 mmol) of 4-fluorobenzaldehyde, 48.4 g (483 mmol) of 1-methylpiperazine and 22.3 g (161 mmol) of potassium carbonate were added to 50 ml of dimethylformamide, and the mixture was heated at 130° C. for 36 hours. The mixture was subsequently concentrated under reduced pressure. The residue was partitioned between ethyl acetate and 2 M hydrochloric acid. The aqueous phase was separated off and made alkaline using aqueous sodium bicarbonate solution. This aqueous phase was extracted with ethyl acetate, and the organic phase was separated off, dried and concentrated under reduced pressure. This gave 48.7 g of the intermediate.

b) Ethyl 2-(4-(4-methylpiperazin-1-yl)phenyl)benzimidazole-4-carboxylate 1.5 g (8.3 mmol) of ethyl 2,3-diaminobenzoate and 2.2 g (10.8 mmol) of the intermediate 8a were reacted by the method of procedure 6a, giving, after purification by silica gel chromatography, 2.8 g of the product.

c) 2-(4-(4-Methylpiperazin-1-yl)phenyl)benzimidazole-4-carbohydrazide

By the method of procedure 6b, 1.35 g (3.7 mmol) of the intermediate 21b were reacted with hydrazine, giving 1.1 g of the product.

d) 2-(4-(4-Methylpiperazin-1-yl)phenyl)benzimidazole-4-carboxamide

By the method of procedure 29c, the intermediate was treated with Raney nickel, giving the product.

$^1$H-NMR (D$_6$-DMSO). δ=2.25 (3H), 2.6 (4H), 3.2 (4H), 7.0-8.1 (9H) and 9.5 (1H) ppm.

EXAMPLE 32

2-(3-(2-Trifluoroacetamidomethylpyrrol-1-yl)phenyl)benzimidazole-4-carboxamide

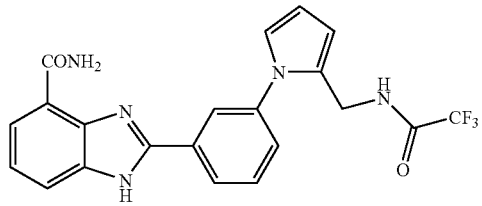

The above compound was prepared analogously to Example 29 from ethyl 2,3-diaminobenzoate, 3-nitrobenzaldehyde and 2,5-dimethoxy-2-(trifluoroacetamidomethyl)tetrahydrofuran.

$^1$H-NMR (D$_6$-DMSO). δ=4.5 (2H), 6.3 (2H), 7.3-8.0 (6H), 9.25 (1H) and 9.8 (1H) ppm.

EXAMPLE 33

2-(3-(3-Formylpyrrol-1-yl)phenyl)benzimidazole-4-carboxamide

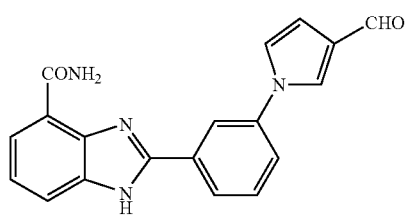

The above compound was prepared analogously to Example 29 from ethyl 2,3-diaminobenzoate, 3-nitrobenzaldehyde and 2,5-dimethoxytetrahydrofuranyl-3-carbaldehyde.

$^1$H-NMR (D$_6$-DMSO). δ=6.8 (2H), 7.3-8.0 (6H), 8.3 (1H), 8.4 (1H), 8.6 (1H), 9.2 (1H) and 9.8 (1H) ppm.

EXAMPLE 34

2-(3-(3-(N,N-Benzylmethylaminomethyl)pyrrol-1-yl)phenyl)benzimidazole-4-carboxamide×2 HCl

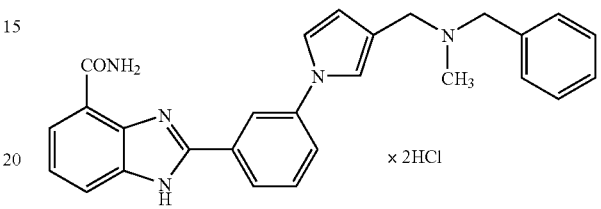

2.0 g (6.0 mmol) of the compound from Example 33, 0.74 g (6.0 mmol) of N-methylbenzylamine and 0.4 ml (6.0 mmol) of glacial acetic acid were dissolved in 100 ml of ethanol. At room temperature, 0.38 g (6.0 mmol) of sodium cyanoborohydride was then added a little at a time, and the entire mixture was stirred at room temperature for 16 h. The mixture was subsequently diluted with aqueous sodium bicarbonate solution and extracted with ethyl acetate. The organic phase was separated off, dried and concentrated under reduced pressure. The residue was purified by silica gel chromatography (mobile phase: ethyl acetate/methanol=10/1). The product obtained in this manner was dissolved in acetone and admixed with isopropanolic hydrogen chloride solution, and the product precipitated out and was filtered off with suction. This gave 0.98 g of the product.

$^1$H-NMR (D$_6$-DMSO). δ=2.6 (3H), 4.1-4.5 (4H), 6.6 (1H), 7.3-8.0 (13H), 8.2 (1H), 8.6 (1H), 9.1 (1H) and 10.8 (1H) ppm.

EXAMPLE 35

2-(3-(2-Aminomethylpyrrol-1-yl)phenyl)benzimidazole-4-carboxamide

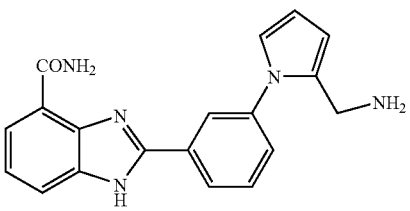

1.0 g (2.3 mmol) of the compound from Example 32 was dissolved in 100 ml of water and admixed with 0.56 g (23.4 mmol) of lithium hydroxide, dissolved in 20 ml of water. The entire mixture was stirred at room temperature for 90 minutes. The organic solvent was subsequently removed under reduced pressure and the resulting aqueous phase was neutralized carefully using dilute hydrochloric acid. The resulting precipitate was filtered off with suction. This gave 0.55 g of the product.

$^1$H-NMR (D$_6$-DMSO). δ=3.8 (2H), 6.2 (2H), 7.0 (1H), 7.35 (1H), 7.6-8.1 (5H), 8.3 (1H), 9.35 (1H) and 9.5 (1H) ppm.

EXAMPLE 36

2-(4-(4-Methylpiperazin-1-yl)phenyl)benzimidazole-4-carboxamide×3 HCl

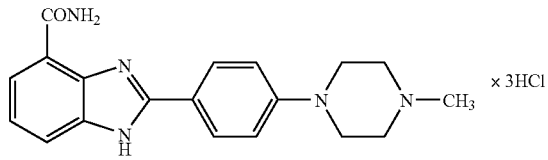

0.25 g of the product from Example 31 was dissolved in 25 ml of ethyl acetate/tetrahydrofuran (4/1) and admixed dropwise with ethereal hydrochloric acid. The resulting precipitate was treated with acetone and filtered off with suction. This gave 0.25 g of the product.

$^1$H-NMR (D$_6$-DMSO). δ=2.75 (3H), 3.1-3.4 (4H), 4.0-4.4 (4H), 7.25 (2H), 7.5 (1H), 7.9-8.1 (4H), 8.3 (2H), 9.0 (broad) and 11.5 (broad) ppm.

EXAMPLE 37

2-(4-(4-tert-Butyloxypiperazin-1-yl)phenyl)benzimidazole-4-carboxamide $^1$H-NMR (D$_6$-DMSO). δ=1.4 (9H), 3.3 (4H), 3.5 (4H), 7.2 (1H), 7.3 (1H), 7.7 (1H), 7.75 (1H), 7.8 (1H), 8.2 (2H), 9.4 (1H) and 12.5 ppm.

EXAMPLE 38

2-(4-(piperazin-1-yl)phenyl)benzimidazole-4-carboxamide×2 HCl $^1$H-NMR (D$_6$-DMSO). δ=3.3 (4H), ca. 3.7 (4H), 7.3 (2H), 7.6 (1H), 7.9-8.0 (3H), 8.3 (2H), 8.7 (1H) and 9.5 (broad) ppm.

EXAMPLE 39

2-(3-(2-(Aminomethyl)pyrrol-1-yl)phenyl)benzimidazole-4-carboxamide×2 HCl $^1$H-NMR (D$_2$O). δ=4.25 (2H), 6.4 (1H), 6.6 (1H), 7.1 (1H), 7.4 (1H), 7.6 (1H), 7.7-7.8 (3H), 7.9 (1H) and 8.0 (1H) ppm.

EXAMPLE 40

2-(4-(3-Formylpyrrol-1-yl)phenyl)benzimidazole-4-carboxamide $^1$H-NMR (D$_6$-DMSO). δ=6.7 (1H), 7.3 (1H), 7.7-8.0 (7H), 8.4 (2H), 9.4 (1H), 9.8 (1H) and 13.5 (broad) ppm.

EXAMPLE 41

2-(4-(3-(N,N-Benzylmethylaminomethyl)pyrrol-1-yl)phenyl)benzimidazole-4-carboxamide×2 HCl MS: m/e=435 (M$^+$).

EXAMPLE 42

2-(4-(3-(N,N-Diethylaminomethyl)pyrrol-1-yl)phenyl)benzimidazole-254-carboxamide×2 HCl $^1$H-NMR (D$_6$-DMSO). δ=1.3 (6H), 3.1 (4H), 4.2 (2H), 6.6 (1H), 7.5 (1H), 7.75 (1H), 7.8-8.0 (6H), 8.5 (2H), 9.1 (1H) and 10.4 (1H) ppm.

EXAMPLE 43

2-(4-(3-(4-Methylpiperazin-1-ylmethyl)pyrrol-1-yl)phenyl)benzimidazole-4-carboxamide $^1$H-NMR (D$_6$-DMSO). δ=2.1 (3H), 2.2-2.5 (8H), 3.35 (2H), 6.2 (1H), 7.3-8.0 (7H), 8.3 (2H) and 9.4 (broad) ppm.

EXAMPLE 44

2-(4-(3-(4-Benzylpiperazin-1-ylmethyl)pyrrol-1-yl)phenyl)benzimidazole-4-carboxamide $^1$H-NMR (D$_6$-DMSO). δ=2.2-2.6 (8H), 3.4 (2H), 3.5 (2H), 6.2 (1H), 7.2-8.0 (13H), 8.3 (2H), 9.4 (1H) and 13.4 (broad) ppm.

EXAMPLE 45

2-(4-(3-(Piperidin-1-ylmethyl)pyrrol-1-yl)phenyl)benzimidazole-4-carboxamide $^1$H-NMR (D$_6$-DMSO). δ=1.3-1.6 (6H), 2.3 (4H), 3.3 (2H), 6.2 (1H), 7.3-8.0 (8H), 8.3 (2H) and 9.4 (broad) ppm.

EXAMPLE 46

2-(4-(4-Benzylpiperazin-1-yl)phenyl)benzimidazol-4-carboxamide 3×[sic]HCl $^1$H-NMR (D$_6$-DMSO). δ=3.2 (4H), 4.2 (4H), 4.5 (2H), 7.2 (2H), 7.4-8.0 (9H), 8.2 (2H), 9.0 (1H) and 11.8 (broad) ppm.

EXAMPLE 47

2-(4-(4-Cyclohexylpiperazin-1-yl)phenyl)benzimidazole-4-carboxamide $^1$H-NMR (D$_6$-DMSO). δ=1.1-1.9 (10H), 2.7 (4H), 3.2 (4H), 4.1 (1H), 7.1 (2H), 7.25 (1H), 7.7 (2H), 7.8 (1H), 8.0 (2H), 9.4 (1H) and ca. 13(broad) ppm.

EXAMPLE 48

2-(4-(4-Ethylpiperazin-1-yl)phenyl)benzimidazole-4-carboxamide $^1$H-NMR (D$_6$-DMSO). δ=1.0 (3H), 2.4 (2H), 2.5 (4H), 3.2 (4H), 7.0-7.3 (3H), 7.6-7.9 (2H), 8.0 (2H), 9.4 (1H) and ca. 13(broad) ppm.

EXAMPLE 49

2-(4-(4-n-Butylpiperazin-1-yl)phenyl)benzimidazole-4-carboxamide $^1$H-NMR (D$_6$-DMSO). δ=0.9 (3H), 1.2-1.6 (4H), 2.3 (2H), 3.2-3.5 (8H), 7.1 (2H), 7.3 (1H), 7.6-7.9 (3H), 8.1 (2H), 9.5 (1H) and 13(broad) ppm.

EXAMPLE 50

2-(4-(4-Diphenylmethylpiperazin-1-yl)phenyl)benzimidazole-4-carboxamide $^1$H-NMR (D$_6$-DMSO). δ=2.5 (4H), 3.2 (4H), 4.3 (1H), 7.0-7.9 (16H), 8.1 (2H), 9.4 (1H) and ca. 13(broad) ppm.

EXAMPLE 51

2-(2-Methyl-4-piperazin-1-ylphenyl)benzimidazole-4-carboxamide 3×[sic]HCl

MS: m/e=335(M$^+$).

EXAMPLE 52

2-(3-piperazin-1-ylphenyl)benzimidazole-4-carboxamide 3×HCl [sic]

$^1$H-NMR (D$_6$-DMSO). δ=3.2 (4H), 3.6 (2H), 7.2-7.6 (3H), 7.7-8.0 (4H), 8.9 (broad) and 9.5 (broad) ppm.

EXAMPLE 53

2-(4-(4-Isopropylpiperazin-1-yl)phenyl)benzimidazole-4-carboxamide $^1$H-NMR (D$_6$-DMSO). δ=1.0 (6H), 2.7 (4H), 2.8 (1H), 3.3 (4H), 7.1 (2H), 7.2 (1H), 7.5-7.9 (3H), 8.05 (2H), 9.4 (1H) and 13(broad) ppm.

EXAMPLE 54

2-(4-(4-tert-Butyloxycarbonylhomopiperazin-1-yl)phenyl)-benzimidazole-4-carboxamide $^1$H-NMR (D$_6$-DMSO). δ=1.1-1.3 (9H), 1.9 (2H), 3.1-3.9 (8H), 6.9 (2H), 7.2 (1H), 7.7-7.9 (3H), 8.0 (2H), 9.5 (1H) and ca. 13(broad) ppm.

EXAMPLE 55

2-(4-(Homopiperazin-1-yl)phenyl)benzimidazole-4-carboxamide $^1$H-NMR (D$_6$-DMSO). δ=2.1 (2H), 3.1 (2H), 3.2 (2H), 3.7 (2H), 3.9 (2H), 7.0 (2H), 7.5 (1H), 7.8-8.0 (3H), 8.2 (2H), 8.7 (broad) and 9.3 (broad) ppm.

EXAMPLE 56

2-(4-(4-(Piperidin-1-yl)piperidin-1-yl)phenyl)benzimidazole-4-carboxamide $^1$H-NMR (D$_6$-DMSO). δ=1.7-1.9 (8H), 2.2 (2H), 2.8-2.9 (3H), 3.3 (4H), 4.1 (2H), 7.1 (2H), 7.3 (1H), 7.7 (1H), 7.75 (1H), 7.8 (1H), 8.1 (2H), 9.4 (1H) and 13.2 (broad) ppm.

EXAMPLE 57

2-(4-(3-Aminopyrroldin-1-yl)phenyl)benzimidazole-4-carboxamide×2 HCl

MS: m/e=321 (M$^+$).

EXAMPLE 58

2-(4-(4-Benzylhomopiperazin-1-yl)phenyl)benzimidazole-4-carboxamide

EXAMPLE 59

2-(4-(4-Methylhomopiperazin-1-yl)phenyl)benzimidazole-4-carboxamide

EXAMPLE 60

2-(4-(4-Ethylhomopiperazin-1-yl)phenyl)benzimidazole-4-carboxamide

EXAMPLE 61

2-(4-(4-Isopropylhomopiperazin-1-yl)phenyl)benzimidazole-4-carboxamide

EXAMPLE 62

2-(4-(4-Butylhomopiperazin-1-yl)phenyl)benzimidazole-4-carboxamide

EXAMPLE 63

Synthesis of 2-phenylbenzimidazole-4-carboxamide a) 2,3-Diaminobenzamide×2 hydrochloride At room temperature, a solution of 200 g (1.11 mol) of ethyl 2,3-diaminobenzoate in 1500 ml of 1-butanol was carefully admixed with 400 ml of hydrazine hydrate. The mixture was heated at 100° C. for 15 hours. The batch was subsequently concentrated to a third of its volume. This solution was slowly added dropwise to a suspension of about 200 g of Raney nickel in 500 ml of water and 1000 ml of dimethylformamide. The mixture was heated at 100° C. for 2 hours. After cooling to 10° C., the catalyst was removed and the filtrate was concentrated under reduced pressure. The resulting oil was dissolved in 500 ml of methanol and admixed with diethyl ether. The precipitate was separated off and the filtrate was concentrated again. A solution of the resulting oil in methanol was, under reflux, admixed with hydrogen chloride/isopropanol. The precipitate that formed on cooling was filtered off with suction, suspended in diethyl ether and filtered off with suction again. This gave 172.2 g of the product.

b) 2-Phenylbenzimidazole-4-carboxamide

At room temperature, 1.68 g (7.5 mmol) of the product from 1b were added to a solution of 0.84 g (15 mmol) of potassium hydroxide powder in 100 ml of ethanol. After 5 minutes, 1.35 g (22.5 mmol) of glacial acetic acid were added, and a solution of 1 g (9.38 mmol) of benzaldehyde in 20 ml of ethanol was added dropwise over a period of 30 minutes. A solution of 2.59 g (12.97 mmol) of copper(II) acetate in 20 ml of dist. water was then rapidly added dropwise. The mixture was refluxed for 2 hours. The batch was poured into water, made alkaline using concentrated ammonia solution and extracted with ethyl acetate. The organic phase was washed with water and, with addition of activated carbon, dried over magnesium sulfate and concentrated under reduced pressure. The resinous residue was triturated with diethyl ether, and the crystals that separated off were washed with diethyl ether and dried under reduced pressure. This gave 1.5 g of the product.

We claim:

1. A compound of formula I or II

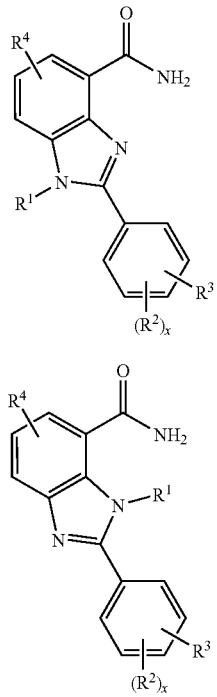

in which
R$^1$ is hydrogen, or branched or unbranched C$_1$-C$_6$-alkyl, it also being possible for one C atom of the alkyl radical to carry OR$^{11}$ or a group R$^5$, where R$^{11}$ is hydrogen or C$_1$-C$_4$ alkyl, and
R$^2$ is hydrogen, chlorine, bromine, iodine, fluorine, CF$_3$, nitro, NHCOR$^{21}$, NR$^{22}$R$^{23}$, OH, O—C$_1$-C$_4$-alkyl, O—C$_1$-C$_4$-alkylphenyl, NH$_2$, or phenyl, it also being possible for the phenyl rings to be substituted by at most two radicals R$^{24}$, and R$^{21}$ and R$^{22}$ independently of one another are hydrogen or C$_1$-C$_4$ alkyl, and R$^{23}$ is hydrogen, C$_1$-C$_4$-alkyl, or phenyl and R$^{24}$ is OH, C$_1$-C$_6$-alkyl, O—C$_1$-C$_6$-alkyl, chlorine, bromine, iodine, fluorine, CF$_3$, nitro or NH$_2$, and
x may be 0, 1 or 2 and
R$^3$ is -D-(F$^1$)$_p$-(E)$_q$-(F$^2$)$_r$-G, where p, q and r may not simultaneously be 0, or R$^3$ is -E-(D)$_u$-(F$^2$)$_s$-(G)$_v$, it also being possible for the radical E to be substituted by one or two radicals A, and if v=0, E is imidazole, pyrrole, pyridine, pyrimidine, piperazine, pyrazine, pyrrolidine or piperidine, or R$^3$ is B and
R$^4$ is hydrogen, chlorine, fluorine, bromine, iodine, branched or unbranched C$_1$-C$_6$-alkyl, OH, nitro, CF$_3$, CN, NR$^{41}$R$^{42}$, NH—CO—R$^{43}$, or O—C$_1$-C$_4$-alkyl, where R$^{41}$ and R$^{42}$ independently of one another are hydrogen or C$_1$-C$_4$-alkyl and
R$^{43}$ is hydrogen, C$_1$-C$_4$-alkyl, C$_1$-C$_4$-alkylphenyl or phenyl, and D is S or O
E is phenyl, imidazole, pyrrole, thiophene, pyridine, pyrimidine, piperazine,
pyrazine, furan, thiazole, isoxazole, pyrrolidine, piperidine, or trihydroazepine, and
F$^1$ is a chain of 1 to 8 carbon atoms, it also being possible for one carbon atom of the chain to carry an OH or O—C$_1$-C$_4$-alkyl group and
F$^2$ is a chain of 1 to 8 carbon atoms, it also being possible for one carbon atom of the chain to carry an OH or C$_1$-C$_4$-alkyl group and
p may be 0 or 1
q may be 0 or 1, and
r may be 0 or 1 and
s may be 0 or 1
u may be 0 or 1
v may be 0 or 1
G may be NR$^{51}$R$^{52}$ or

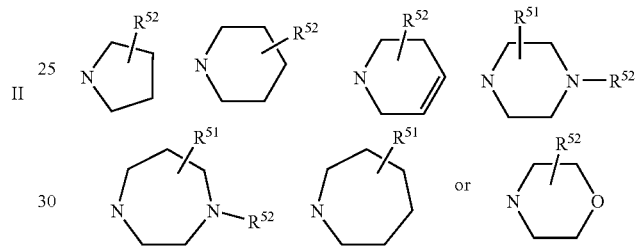

where
R$^{51}$ is hydrogen or branched or unbranched C$_1$-C$_6$-alkyl, or (CH$_2$)$_t$—K
and
R$^{52}$ is hydrogen, branched or unbranched C$_1$-C$_6$-alkyl, phenyl,

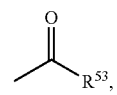

—SO$_2$R$^{53}$, —(C=N)—R$^{53}$, —(C=N)—NHR$^{53}$ or —CO—NHR$^{53}$
in which
R$^{53}$ may be branched or unbranched O—C$_1$-C$_6$-alkyl, phenyl, or branched or unbranched C$_1$-C$_4$-alkylphenyl, where in the case of R$^{52}$ and R$^{53}$, independently of one another, one hydrogen of the C$_1$-C$_6$-alkyl radical may be replaced by one of the following radicals: OH, O—C$_1$-C$_4$-alkyl, cyclohexyl, cyclopentyl, tetrahydronaphthyl, cyclopropyl, cyclobutyl, cycloheptyl, naphthyl or phenyl, it also being possible for the phenyls of the radicals R$^{52}$ and R$^{53}$ independently of one another to carry one or two of the following radicals: branched or unbranched C$_1$-C$_6$-alkyl, branched or unbranched O—C$_1$-C$_4$-alkyl, OH, F, Cl, Br, I, CF$_3$, NO$_2$, NH$_2$, COOH, COOC$_1$-C$_4$-alkyl, C$_1$-C$_4$-alkylamino, CCl$_3$, C$_1$-C$_4$-di-alkylamino, SO$_2$—C$_1$-C$_4$-alkyl, SO$_2$-phenyl, CONH$_2$, CONH—C$_1$-C$_4$-alkyl, CONHphenyl, CONH—C$_1$-C$_4$-alkylphenyl, NHSO$_2$—C$_1$-C$_4$-alkyl, NHSO$_2$-phenyl, S—C$_1$-C$_4$alkyl, —O—(C=O)—$C_1$-$C_4$-alkyl,  —O—(C=O)—$C_0$-$C_4$-alkylphenyl, CHO, —$CH_2$—O—$C_1$-$C_4$-alkyl, —$CH_2$O—$C_1$-$C_4$-alkylphenyl, —$CH_2$OH, —SO—$C_1$-$C_4$-alkyl, —SO—$C_1$-$C_4$-alkylphenyl, —$SO_2NH_2$ or —$SO_2NH$—$C_1$-$C_4$-alkyl,
or two radicals form a bridge —O—$(CH_2)_{1,2}$—O—,
B may be

[ring structures with $R^7$, $R^5$, $R^9$ substituents: pyrrolidine, piperidine, tetrahydropyridine, piperazine, diazepane, morpholine]

and
A may be hydrogen, chlorine, bromine, iodine, fluorine, $CF_3$, nitro, OH, O—$C_1$-$C_4$-alkyl, O—$C_1$-$C_4$-alkylphenyl, $NH_2$, branched or unbranched $C_1$-$C_6$-alkyl, CN or NH—CO—$R^{33}$ where $R^{33}$ is hydrogen or $C_1$-$C_4$-alkyl, and
t is 0, 1, 2, 3 or 4 and
K is phenyl, and
$R^5$ may be hydrogen, $C_1$-$C_6$-alkyl, or $NR^7R^9$ and

[ring structures with $R^7$, $R^9$ substituents]

and
$R^7$ is hydrogen, $C_1$-$C_6$-alkyl, $C_1$-$C_4$-alkylphenyl or phenyl, it also being possible for the rings to be substituted by up to two radicals $R^{71}$, and
$R^{71}$ is OH, $C_1$-$C_6$-alkyl, O—$C_1$-$C_4$-alkyl, chlorine, bromine, iodine, fluorine, $CF_3$, nitro, or $NH_2$, and
$R^9$ is hydrogen, $COCH_3$, CO—O—$C_1$-$C_4$-alkyl, $COCF_3$, branched or unbranched $C_1$-$C_6$-alkyl, it being possible for one or two hydrogens of the $C_1$-$C_6$-alkyl radical to be replaced in each case by one of the following radicals: OH, O—$C_1$-$C_4$-alkyl and phenyl, and for the phenyl ring also to carry one or two of the following radicals: iodine, chlorine, bromine, fluorine, branched or unbranched $C_1$-$C_6$-alkyl, nitro, amino, $C_1$-$C_4$-alkylamino, $C_1$-$C_4$-dialkylamino, OH, O—$C_1$-$C_4$-alkyl, CN, $CF_3$, or $SO_2$—$C_1$-$C_4$-alkyl, or a tautomeric form, a possible enantiomeric or diasteriomeric form, a prodrug or pharmacologically tolerated salt thereof.

2. A compound of formula I or II

[Structure I: benzimidazole-carboxamide with $R^4$, $R^1$, $R^3$, $(R^2)_x$ substituents]

[Structure II: benzimidazole-carboxamide with $R^4$, $R^1$, $R^3$, $(R^2)_x$ substituents]

in which
$R^1$ is hydrogen, or branched or unbranched $C_1$-$C_6$-alkyl, it also being possible for one C atom of the alkyl radical to carry $OR^{11}$ or a group $R^5$, where x is 0, 1 or 2,
$R^{11}$ is hydrogen or $C_1$-$C_4$-alkyl, and
$R^2$ is hydrogen, chlorine, fluorine, bromine, iodine, branched or unbranched $C_1$-$C_6$-alkyl, nitro, $CF_3$, CN, $NR^{21}R^{22}$, NH—CO—$R^{23}$, or $OR^{21}$, where
$R^{21}$ and $R^{22}$ are, independently of one another, hydrogen or $C_1$-$C_4$-alkyl, and
$R^{23}$ is hydrogen or $C_1$-$C_4$-alkyl, and
$R^3$ is O—$(CH_2)_o$—$(CHR^{31})_m$—$(CH_2)_n$—$R^5$ where
$R^{31}$ is hydrogen, $C_1$-$C_4$-alkyl, OH or O—$C_1$-$C_4$-alkyl,
m and o are, independently of one another, 0, 1 or 2, and
n is 1, 2, 3 or 4 and
$R^4$ is hydrogen, branched or unbranched $C_1$-$C_6$-alkyl, chlorine, bromine, fluorine, nitro, cyano, $NR^{41}R^{42}$, NH—CO—$R^{43}$, or $OR^{41}$, where
$R^{41}$ and $R^{42}$ are, independently of one another, hydrogen or $C_1$-$C_4$-alkyl, and
$R^{43}$ is $C_1$-$C_4$-alkyl or phenyl, and $R^5$ is $NR^{51}R^{52}$ or one of the following radicals where $R^{51}$ is hydrogen or branched or unbranched $C_1$-$C_6$-alkyl, and $R^{52}$ is hydrogen, or branched or unbranched $C_1$-$C_6$-alkyl, phenyl, or —$SO_2R^{53}$, in which $R^{53}$ is branched or unbranched O—$C_1$-$C_6$-alkyl, phenyl, or branched or unbranched $C_1$-$C_4$-alkylphenyl, where one hydrogen in the $C_1$-$C_6$-alkyl radical in $R^{52}$ and $R^{53}$, independently of one another, optionally replaced by one of the following radicals: OH, O—$C_1$-$C_4$-alkyl, cyclohexyl, cyclopentyl, tetrahydronaphthyl, cyclopropyl, cyclobutyl, cycloheptyl, naphthyl or phenyl, where the phenyls of the $R^{52}$ and $R^{53}$ radicals may also, independently of one another, carry one or two of the following radicals: branched or unbranched $C_1$-$C_6$-alkyl, branched or unbranched O—$C_1$-$C_4$-alkyl, OH, F, Cl, Br, I, $CF_3$, $NO_2$, $NH_2$, CN, COOH, COO—$C_1$-$C_4$-alkyl, $C_1$-$C_4$alkylamino, —$CCl_3$, $C_1$-$C_4$-di-alkylamino, $SO_2$—$C_1$-$C_4$-alkyl, $SO_2$phenyl, $CONH_2$, CONH—$C_1$-$C_4$-alkyl, CONHphenyl, CONH—$C_1$-$C_4$-alkyl-phenyl, $NHSO_2$—$C_1$-$C_4$-alkyl, $NHSO_2$phenyl, S—$C_1$-$C_4$-alkyl, CHO, $CH_2$—O—$C_1$-$C_4$-alkyl, —$CH_2OC_1$-$C_4$-alkyl-phenyl, —$CH_2OH$, —SO—$C_1$-$C_4$-alkyl, —SO—$C_1$-$C_4$-alkyl-phenyl, $SO_2NH_2$ or —$SO_2NH$—$C_1$-$C_4$-alkyl or two radicals form a bridge —O—$(CH_2)_{1,2}$—O—, or a tautomeric form, a possible enantiomeric or diastereomeric form, a prodrug or pharmacologically tolerated salt thereof.

3. A compound of formula I or II in which $R^1$ is hydrogen, or branched or unbranched $C_1$-$C_6$-alkyl, it also being possible for one C atom of the alkyl radical to carry $OR^{11}$ or a group $R^5$, where x is 0, 1 or 2, $R^{11}$ is hydrogen or $C_1$-$C_4$-alkyl, and $R^2$ is hydrogen, chlorine, fluorine, bromine, iodine, branched or unbranched $C_1$-$C_6$-alkyl, nitro, $CF_3$, CN, $NR^{21}R^{22}$, NH—CO—$R^{23}$, or $OR^{21}$, where $R^{21}$ and $R^{22}$ are, independently of one another, hydrogen or $C_1$-$C_4$-alkyl, and $R^{23}$ is hydrogen, $C_1$-$C_4$-alkyl or phenyl, and $R^3$ is and $R^{31}$ is hydrogen, CHO or —O—$(CH_2)_o$—$(CHR^{32})_m$—$(CH_2)_n$—$R^5$ where $R^{32}$ is hydrogen, $C_1$-$C_4$-alkyl, OH or $C_1$-$C_4$-alkyl, m and o independently of one another are 0, 1 or 2 and n is 1, 2, 3 or 4, and $R^4$ is hydrogen, or branched or unbranched $C_1$-$C_6$-alkyl, chlorine, bromine, fluorine, nitro, cyano, $NR^{41}R^{42}$, NH—CO—$R^{43}$, or $OR^{41}$, where $R^{41}$ and $R^{42}$ are, independently of one another, hydrogen or $C_1$-$C_4$-alkyl and $R^{43}$ is $C_1$-$C_4$-alkyl or phenyl, and $R^5$ is $NR^{51}R^{52}$ or one of the radicals below

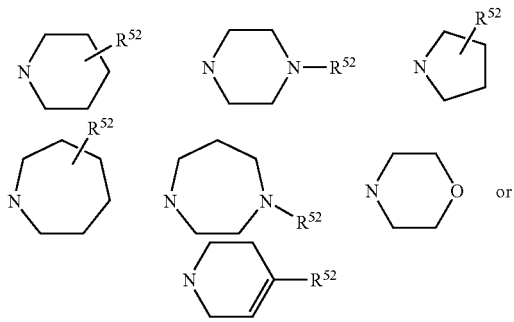

where
$R^{51}$ is hydrogen or branched or unbranched $C_1$-$C_6$-alkyl, and
$R^{52}$ is hydrogen, $COCH_3$, CO—O—$C_1$-$C_4$-alkyl, $COCF_3$, or branched or unbranched $C_1$-$C_6$-alkyl, it being possible for one hydrogen of the $C_1$-$C_6$-alkyl radical to be replaced by one of the following radicals: OH, O—$C_1$-$C_6$-alkyl or phenyl and for the phenyl ring also to carry one or two of the following radicals: chlorine, bromine, fluorine, branched or unbranched $C_1$-$C_4$-alkyl, nitro, amino, $C_1$-$C_4$-alkylamino, $C_1$-$C_4$-dialkylamino, OH, O—$C_1$-$C_4$-alkyl, CN, or $SO_2$—$C_1$-$C_4$-alkyl, or a tautomeric form, or a possible enantiomeric or diasteriomeric form, or a prodrug or pharmacologically tolerated salt thereof.

4. A compound as claimed in claim 1, 2 or 3 where $R^2$ is in position 3 and $R^3$ is in position 4 or $R^2$ is in position 4 and $R^3$ is in position 3 relative to the benzimidazole ring.

5. A compound as claimed in claim 1, 2 or 3 where $R^1$ and $R^4$ are hydrogen.

6. A compound as claimed in claim 1, 2 or 3 where $R^2$ is hydrogen, or branched or unbranched $C_1$-$C_6$-alkyl, nitro, CN, $NH_2$, or O—$C_1$-$C_4$-alkyl.

7. A compound of formula I or II

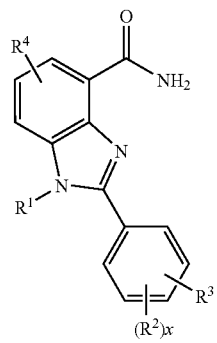

I

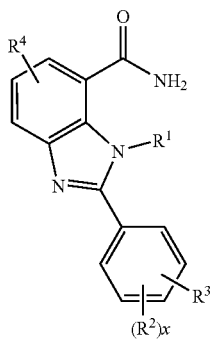

II in which
$R^1$ is hydrogen, or branched or unbranched $C_1$-$C_6$-alkyl it also being possible for one C atom of the alkyl radical to carry $OR^{11}$ or a group $R^5$, where x is 0, 1 or 2,
$R^{11}$ is hydrogen or $C_1$-$C_4$-alkyl and
$R^2$ is hydrogen, chlorine, fluorine, bromine, iodine, branched or unbranched $C_1$-$C_6$-alkyl, nitro, $CF_3$, CN, $NR^{21}R^{22}$, NH—CO—$R^{23}$, or $OR^{21}$, where
$R^{21}$ and $R^{22}$ are, independently of one another, hydrogen or $C_1$-$C_4$-alkyl, and
$R^{23}$ is hydrogen, $C_1$-$C_4$-alkyl or phenyl, and
$R^3$ is
(i)

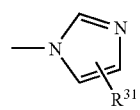

$R^{31}$ is hydrogen or —$(CH_2)_p$—$R^5$, where
p is 1 or 2 and
$R^{52}$ may be hydrogen, or branched or unbranched $C_1$-$C_6$-alkyl, where one hydrogen of the $C_1$-$C_6$-alkyl radical may be replaced by one of the following radicals: OH, O—$C_1$-$C_4$-alkyl and phenyl, and where the phenyl ring may also carry one or two of the following radicals: chlorine, bromine, fluorine, branched or unbranched $C_1$-$C_4$-alkyl, nitro, amino, $C_1$-$C_4$-alkylamino, $C_1$-$C_4$-dialkylamino, OH, O—$C_1$-$C_4$-alkyl, CN, or $SO_2$—$C_1$-$C_4$-alkyl;
Or
(ii) $R^3$ is

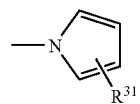

$R^{31}$ is hydrogen or —$(CH_2)_p$—$R^5$, where
p is 1 or 2 and
$R^{52}$ may be hydrogen, or branched or unbranched $C_1$-$C_6$-alkyl, where one hydrogen of the $C_1$-$C_6$-alkyl radical may be substituted by one of the following radicals: OH, O—$C_1$-$C_4$-alkyl and phenyl, and where the phenyl ring may also carry one or two of the following radicals: chlorine, bromine, fluorine, branched or unbranched $C_1$-$C_4$-alkyl, nitro, amino, $C_1$-$C_4$-alkylamino, $C_1$-$C_4$-dialkylamino, OH, O—$C_1$-$C_4$-alkyl, CN, or $SO_2$—$C_1$-$C_4$-alkyl;
Or
(iii) $R^3$ is

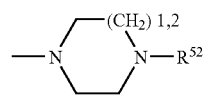

where $R^{52}$ is hydrogen, or branched or unbranched $C_1$-$C_6$-alkyl, where one hydrogen of the $C_1$-$C_6$-alkyl radical may be replaced by one of the following radicals: OH, O—$C_1$-$C_4$-alkyl and phenyl, and where the phenyl ring may also carry one or two of the following radicals: chlorine, bromine, fluorine, branched or unbranched $C_1$-$C_4$-alkyl, nitro, amino, $C_1$-$C_4$-alkylamino, $C_1$-$C_4$-dialkylamino, OH, O—$C_1$-$C_4$-alkyl, CN, or $SO_2$—$C_1$-$C_4$-alkyl, $R^4$ is hydrogen, or branched or unbranched $C_1$-$C_6$-alkyl, chlorine, bromine, fluorine, nitro, cyano, $NR^{41}R^{42}$, NH—CO—$R^{43}$, or $OR^{41}$, where $R^{41}$ and $R^{42}$ are, independently of one another, hydrogen or $C_1$-$C_4$-alkyl and $R^{43}$ is $C_1$-$C_4$-alkyl or phenyl, and $R^5$ is $NR^{51}R^{52}$ or one of the radicals below

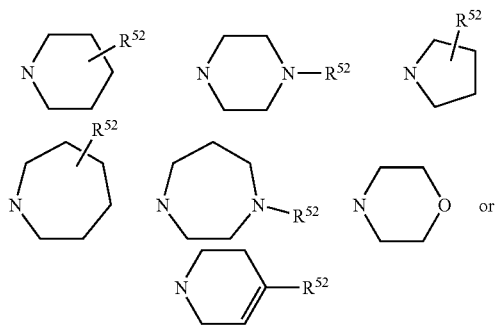

where $R^{51}$ is hydrogen or branched or unbranched $C_1$-$C_6$-alkyl, or a tautomeric form, a possible enantiomeric or diasteriomeric form, a prodrug or pharmacologically tolerated salt thereof.

8. A compound as claimed in claim 1, where $R^3$ is -D-$(F^1)_p$-$(E)_q$-$(F^2)_r$-G, where D is O, $F^1$ is a $C_1$-$C_4$ carbon chain, p is 1, q is 0 and r is 0.

9. A compound as claimed in claim 1, where $R^5$ is a 6-membered ring selected from

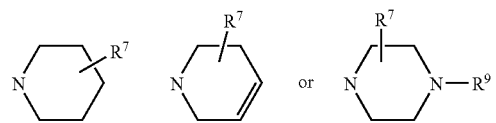

and $R^{52}$ is a phenyl ring.

10. A drug comprising besides conventional vehicles and ancillary substances a compound as claimed in claim 1.

11. A method for treating a disorder in which pathologically elevated PARP activities occur, said method comprising administering an effective amount of a compound of the formula I as claimed in claim 1 to a mammal suffering from said disorder wherein the disorder is stroke or craniocerebral trauma.

12. A method for treating ischemia, said method comprising administering an effective amount of a compound of the formula I as claimed in claim 1 to a mammal suffering from ischemia.

13. A method for treating epilepsy, said method comprising administering an effective amount of a compound of the formula I as claimed in claim 1 to a mammal suffering from epilepsy.

14. A method for treating damage to the kidneys after renal ischemia, damage caused by drug therapy or damage resulting after kidney transplants, said method comprising administering an effective amount of a compound of the formula I as claimed in claim 1 to a mammal suffering from damage to the kidneys after renal ischemia, damage caused by drug therapy or damage resulting after kidney transplants.

15. A method for treating damage to the heart after cardiac ischemia, said method comprising administering an effective amount of a compound of the formula I as claimed in claim 1 to a mammal suffering from damage to the heart after cardiac ischemia.

16. A method for treating a microinfarct said method comprising administering an effective amount of a compound of the formula I as claimed in claim 1 to a mammal suffering from a microinfarct.

17. A method for treating under vascularization of critically narrowed coronary arteries said method comprising administering an effective amount of a compound of the formula I as claimed in claim 1 to a mammal suffering from under vascularization of critically narrowed coronary arteries.

18. A method for treating an acute myocardial infarct and damage during and after medical or mechanical lysis thereof, said method comprising administering an effective amount of a compound of the formula I as claimed in claim 1 to a mammal suffering from an acute myocardial infarct and damage during and after medical or mechanical lysis thereof.

19. A method for treating sepsis of multiorgan failure, said method comprising administering an effective amount of a compound of the formula I as claimed in claim 1 to a mammal suffering from sepsis of multiorgan failure.

20. A method for treating diabetes mellitus, said method comprising administering an effective amount of a compound of the formula I as claimed in claim 1 to a mammal suffering from diabetes mellitus.

* * * * *

UNITED STATES PATENT AND TRADEMARK OFFICE
CERTIFICATE OF CORRECTION

PATENT NO.     : 7,781,596 B1
APPLICATION NO. : 09/830992
DATED          : August 24, 2010
INVENTOR(S)    : Lubisch et al.

It is certified that error appears in the above-identified patent and that said Letters Patent is hereby corrected as shown below:

Column 43, line 25, claim 1: "$(R^2)_x$" to read as --$(R^2)x$--

Column 43, line 39, claim 1: "$(R^2)_x$" to read as --$(R^2)x$--

Column 43, line 45, claim 1: "$C_1$-$C_4$alkyl" to read as --$C_1$-$C_4$-alkyl--

Column 43, line 51, claim 1: "$C_1$-$C_4$alkyl" to read as --$C_1$-$C_4$-alkyl--

Column 44, line 28, claim 1: "$R^{51}$" to read as --$R^{52}$--

Column 44, line 62, claim 1: "$NO_2,NH_2$" to read as --$NO_2$, $NH_2$--

Column 44, line 65, claim 1: "CONHphenyl" to read as --CONH-phenyl--

Column 44, line 67, claim 1: "$C_4$alkyl" to read as --$C_4$-alkyl--

Column 45, line 26, claim 1: insert -- 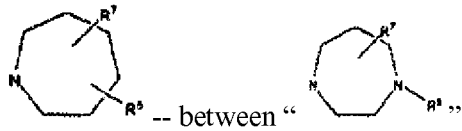 -- between " 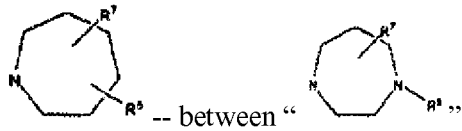 "

and "or 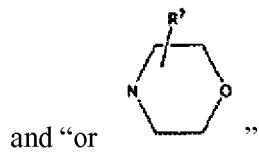 "

Column 46, line 8, claim 1: "diasteriomeric" to read as --diastereomeric--

Column 47, line 37, claim 2: "$R^{53}$," to read as --$R^{53}$ are,--

Column 47, line 47, claim 2: "$C_4$alkylamino" to read as --$C_4$-alkylamino--

Column 47, line 48, claim 2: "$SO_2$phenyl" to read as --$SO_2$-phenyl--

Signed and Sealed this
Thirteenth Day of March, 2012

David J. Kappos
*Director of the United States Patent and Trademark Office*

CERTIFICATE OF CORRECTION (continued)
U.S. Pat. No. 7,781,596 B1

Column 47, line 49, claim 2: "CONHphenyl" to read as --CONH-phenyl--

Column 47, line 50, claim 2: "NHSO$_2$phenyl" to read as --NHSO$_2$-phenyl--

Column 47, line 65, claim 2: "diasteriomeric" to read as --diastereomeric--

Column 49, line 28, claim 3: "diasteriomeric" to read as --diastereomeric--

Column 50, line 33, claim 7: "Or" to read as --or--

Column 50, line 53, claim 7: "Or" to read as --or--

Column 51, line 28, claim 7: "diasteriomeric" to read as --diastereomeric--